(12) United States Patent
Conte et al.

(10) Patent No.: US 7,993,348 B2
(45) Date of Patent: Aug. 9, 2011

(54) CURVED ACETABULAR POSITIONER, IMPACTOR AND REAMER HANDLE

(75) Inventors: John Conte, Prospect Park, PA (US); Joseph C. Jenkins, II, Lindenhurst, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1139 days.

(21) Appl. No.: 11/641,599

(22) Filed: Dec. 19, 2006

(65) Prior Publication Data
US 2007/0293869 A1 Dec. 20, 2007

Related U.S. Application Data

(60) Provisional application No. 60/752,154, filed on Dec. 20, 2005.

(51) Int. Cl.
*A61F 2/46* (2006.01)
(52) U.S. Cl. .................. 606/91; 606/79; 606/81; 606/99
(58) Field of Classification Search ................. 606/86 R, 606/89, 91, 99, 79–81
See application file for complete search history.

(56) References Cited

U.S. PATENT DOCUMENTS

| 4,023,572 A | 5/1977 | Weigand et al. |
| 5,658,290 A | 8/1997 | Lechot |
| 6,475,243 B1 | 11/2002 | Sheldon et al. |
| 7,785,329 B2 * | 8/2010 | Lechot et al. ................... 606/81 |
| 2003/0050645 A1 | 3/2003 | Parker et al. |
| 2003/0229356 A1 | 12/2003 | Dye |
| 2004/0087958 A1 | 5/2004 | Myers et al. |
| 2004/0153063 A1 | 8/2004 | Harris |
| 2005/0038443 A1 | 2/2005 | Hedley et al. |
| 2005/0216022 A1 | 9/2005 | Lechot et al. |
| 2006/0058885 A1* | 3/2006 | Wozencroft ............... 623/22.12 |
| 2006/0149285 A1 | 7/2006 | Burgi et al. |

FOREIGN PATENT DOCUMENTS

WO  WO 2005/044153  *  5/2005

* cited by examiner

*Primary Examiner* — Thomas C Barrett
*Assistant Examiner* — Matthew Lawson
(74) *Attorney, Agent, or Firm* — Lerner, David, Littenberg, Krumholz & Mentlik, LLP

(57) ABSTRACT

An acetabular instrument has a handle portion having one or more solid nonflexible drive shaft elements therethrough. The shaft elements are connected by a U-joint at one of both ends to form a flexible curved drive shaft. One end of a solid shaft element is connected to a knob so that rotation of the knob drives the flexible shaft. The flexible shaft is housed within a hollow curved body preferably made of stainless steel. One end of the curved body it is connected to the handle portion and at the other end to an acetabular cup or acetabular reamer holder. The reamer holder is rotatably driven by the flexible drive shaft. The knob may be made so that it may receive blows from a mallet allowing the instrument to be used as an impactor. The drive shaft may be used to actuate a locking mechanism within the cup or reamer holder which connects the reamer cup to the instrument.

19 Claims, 26 Drawing Sheets

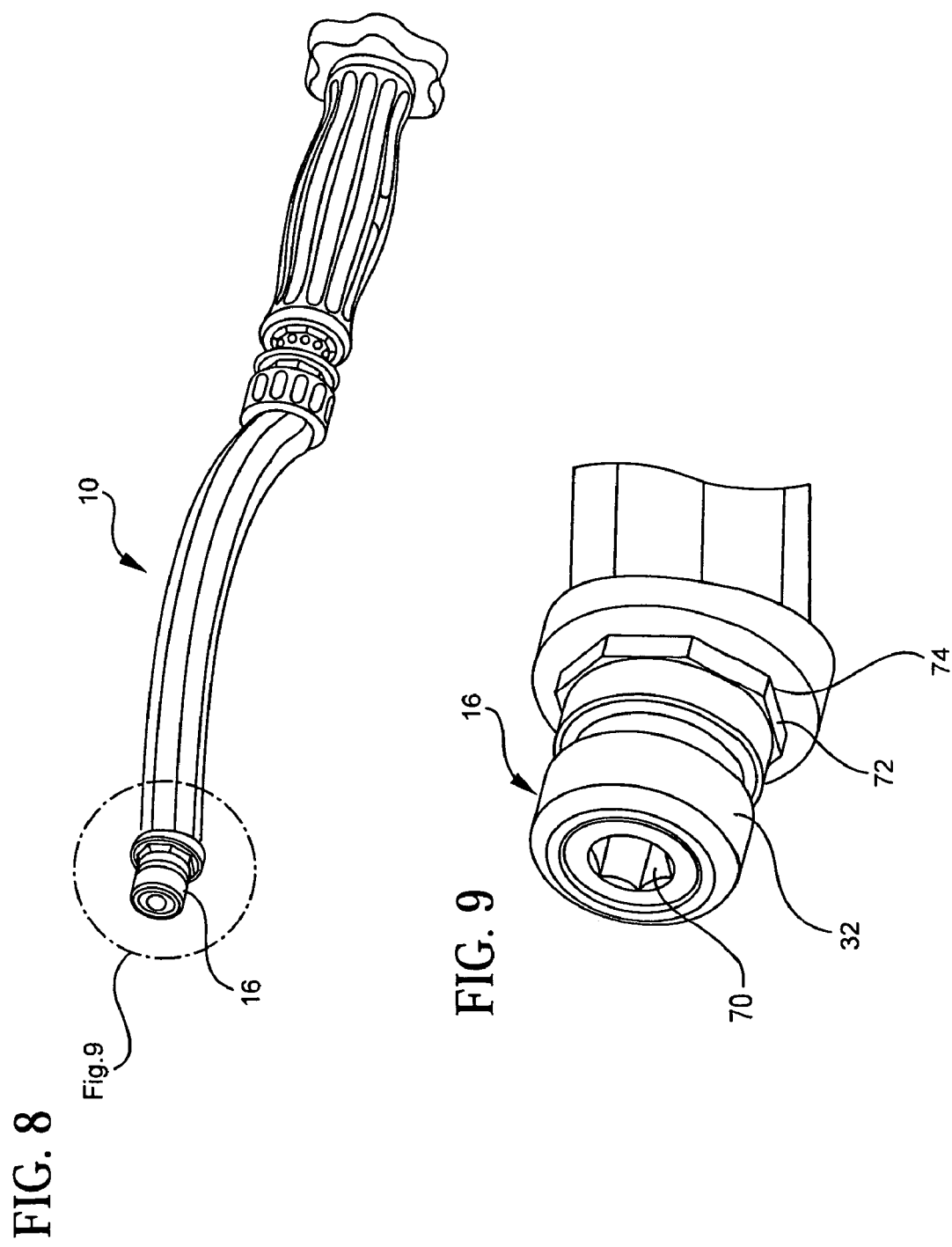

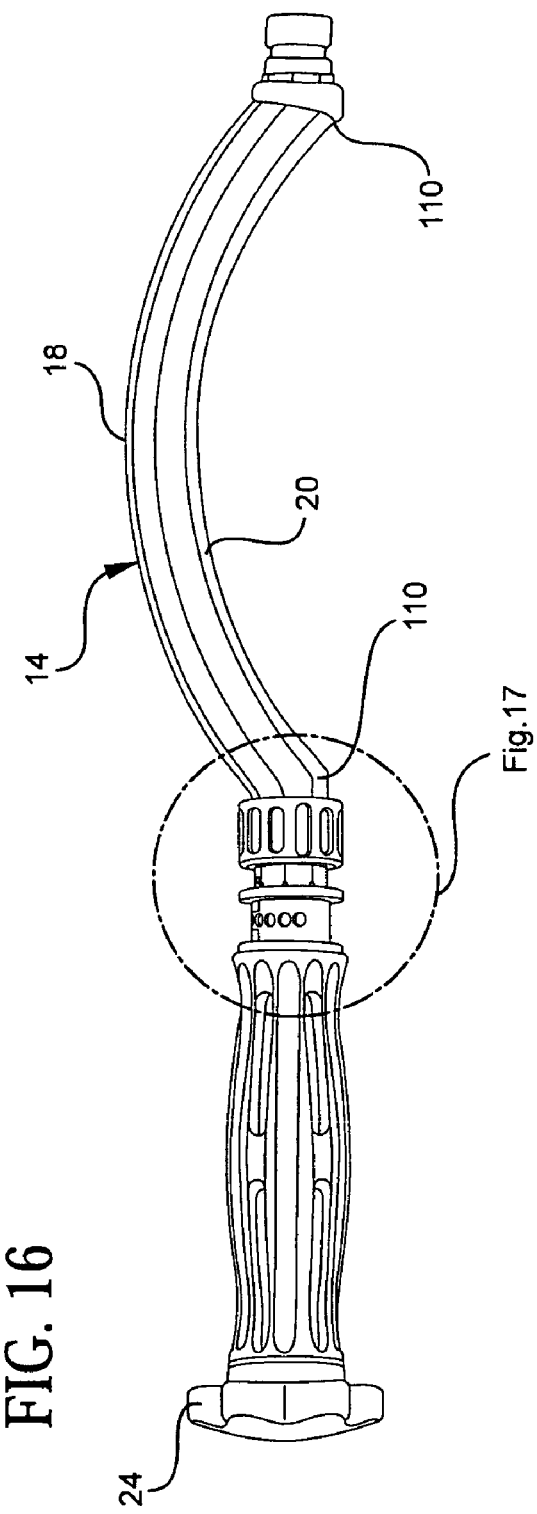
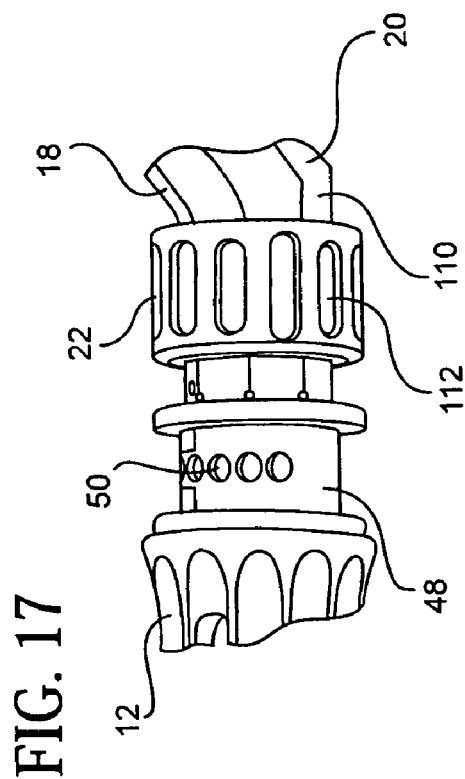
FIG. 16
FIG. 17

CURVED ACETABULAR POSITIONER, IMPACTOR AND REAMER HANDLE

CROSS-REFERENCE TO RELATED APPLICATIONS

This application claims the benefit of the filing date of U.S. Provisional Patent Application No. 60/752,154 filed Dec. 20, 2005, the disclosure of which is hereby incorporated herein by reference.

BACKGROUND OF THE INVENTION

Over time the surgical technique for total hip replacements has evolved. Incision length has been reduced over time as surgeons become more comfortable operating with limited visibility. The location of the incision has also been changing as surgeons have developed and implemented different approaches to the joint. These two factors have increased the challenges of implanting acetabular implants in the correct orientation as the acetabular tools impinge on bone or soft tissue around the perimeter of the incision.

Acetabular implants normally consist of a shell or cup and a modular insert that fits within the shell and acts as a bearing surface for the femoral head. While modular shells and inserts are preferred for a number of reasons, there is an application where shells and inserts are combined preoperatively in a monoblock construction. Such shells and inserts are shown in U.S. Pat. No. 6,475,243, the disclosure of which is incorporated herein by reference.

Acetabular instruments normally consist of a series of reamers, a reamer handle, a shell positioner/impactor and an insert positioner/impactor. In addition, alignment guides are often attached to the reamer handle and shell positioner/impactor in order to facilitate alignment. A typical reamer is shown in U.S. Pat. Nos. 4,023,572 and 5,658,290.

Shells are implanted into an acetabulum after the acetabulum has been prepared to receive the shell through the use of a series of reamers increasing in size. The shells are aligned in the acetabulum according to two angles: abduction and anteversion. The combination of these two angles creates the axis that the shell should be aligned and impacted on.

Traditionally acetabular reamer handles and shell and insert positioner/impactors had straight shafts. In some surgeries the size or location of the incision results in the shaft of these instruments impinging on the side of the incision before the preferred abduction/anteversion axis is achieved. In these cases the surgeon has to force the soft tissue or bone out of the way, increase the length of the incision, or accept the abduction/anteversion angle that can be achieved. None of these options are preferred.

One method for avoiding impingement between these acetabular instruments and the incision is to create inline or offset curved acetabular instruments. "Inline" refers to an acetabular instrument that has a curved section between the two ends of the instrument that lie on the same axis. Typically, the first end includes a hex drive for connection to a rotary power service (drill) and a second end which has a holder for an acetabular instrument such as a reamer or the acetabular shell itself. "Offset" refers to an acetabular instrument that has a curved section between the two ends of the instrument that lie on different axis. The curved section should begin as quickly as possible after the attachment to the reamer, shell or insert in order to minimize the impingement.

An inline curved or offset acetabular instrument is preferred for a number of reasons. Typically, the surgeon is used to operating with inline straight instruments. By maintaining the inline aspect of the design, the ergonomics of the instrument remain the same and the surgeon learning curved is reduced. In addition an inline instrument allows for all forces to be projected in line or parallel to the correct axis. Finally, an inline instrument allows for alignment guides to be indexed around the axis of the instrument without changing its position in relation to the implant. In-line or offset reamers/impactors are shown in U.S. patent publications 2003/0050645, 2003/0229356, 2004/0153063, 2004/0087958, 2005/0038443 and 2005/0216022.

The introduction of a curve into acetabular instrument introduces various challenges to designing a reamer handle. Reamer handles are used to transmit torque and axial load from a power source, such as a rotary power source to the reamer. This is accomplished through the use of a straight shaft with a fitting that mates with the power source on one end and a locking mechanism that connects to the reamer on the other end. The torque is transmitted from the power source to the fitting to the shaft to the locking mechanism and finally to the reamer. The axial force is transmitted from the surgeon to the power source to the shaft to the locking mechanism to the reamer.

The same holds true for the shell positioner/impactors. Shells are typically connected to positioner/impactors by threading the two together with torque. This is accomplished through the use of a straight shaft with a handle that the surgeon grips on one end and a threaded fitting that connects to the shell on the other end. The torque is transmitted from the surgeon to the handle to the shaft to the threaded fitting to the shell. The axial force is transmitted from the surgeon to the mallet to the handle to the shaft to the threaded fitting to the shell.

With an inline or offset curved acetabular instrument the torque and axial load needs to be transmitted around a curve. In addition, the curved body that transmits the axial load cannot also transmit the torque. This is because the curved body would impinge on the incision if one tried to rotate it through a full rotation. To solve this problem, a handle having a hollow curved body with a drive train housed internally is provided. The drive train needs to be able to transmit torque through the curved body. This is accomplished through the use of U-joints and/or flexible shafts.

In the case of an offset curved instrument, two u-joints allow the transmission of torque between the two ends of the instrument. In the case of an inline curved instrument a series of U-joints (5-6) or a combination of U-joints (2) and a flexible shaft allows the transmission of torque between the two ends of the instrument. There are many other combinations and permutations of U-joints and flexible shafts that would meet the requirements.

The curved body is preferably machined from a solid block referred to as a monoblock, to produce the curved body rather than using a bent tube. The use of a machined body allows for increased precision of the instrument and drive train. The internal drive-train can easily be removed without the use of tools once a moveable lid is opened. This is because the multiple U-joint drive shaft is flexible and is held at position at the ends within fixed U-joints mounted to the curved body only by mating hex couplings. These couplings may be easily slid apart to disassemble the drive-train from the handle. The monoblock also serves to mount modular navigation and alignment guides such as a typical mechanical guide or a well-known optical navigation tractor. Obviously if no guide is necessary, the mounting position on the monoblock curved body can be left empty.

The modular alignment system can be attached to the body of the instrument preferably adjacent the handle. This alignment system is indexible. This allows the mechanical or optical tracker system to be positioned properly with respect to the typical acetabular cup or shell which has a plurality of screw holes therethrough. The indexible alignment system also allows for left and right positions for the impactor/reamer and allows proper positioning of the curve and minimization of impingement with adjacent soft tissue.

In one possible embodiment a modular cup or reamer holder includes an actuatable release mechanism which can be connected the curved impactor/reamer by a push button mechanism described below. The cup or reamer holder can then be attached and/or disconnected such as by threading a threaded projection on the leading end of the modular holder into a threaded bore in the cup. This can be accomplished by turning a knob at the end of the handle which turns the drive-train which in turn rotates the threaded tip. Disconnection is accomplished by turning the knob at the end of the handle in the opposite direction. The design can be reversed with the actuatable release mechanism being located on the end of the handle. This simplifies the design of the modular cup or reamer holder and reduces cost since only one release mechanism is necessary when multiple holders are used.

If a modular holder is utilized, the cup initially could be threaded onto the holder or tip while disconnected from the curved positioner or impactor. The holder cup combination can then be inserted into the hip joint, perhaps sideways as for a smaller incision, and then reconnected to the curved positioner. The modular holder can be removed from the cup and incision if the curved impactor fails during impaction. The user can disconnect the modular cup holder and utilize a new impactor by reconnecting the impactor end to the modular cup holder or tip.

This modularity also allows a user to have multiple holders designed both for preassembled metal shells and polyethylene or ceramic bearings. Thus one holder can be designed to engage the polyethylene bearing of a preassembled acetabular cup and a second modular holder designed to engage a cup design having an outer shell and a ceramic bearing. Obviously, one-piece prosthetic cups made of polyethylene or ceramic could also be gripped. These modular holders can be supplied as part of a kit which has one positioner/impactor and several holders designed to couple to different implants rather than having multiple positioner/impactors.

The preferred embodiment of the shell positioner/impactor of the present invention uses a series of U-joints. Two U-joints are fixed in the corners (one at each end) of the curved body and a chain composing of preferably four U-joints is assembled between the two end U-joints. The preferred U-joint chain is assembled by connecting two male hex fittings to female counterparts of the two corner U-joints. The U-joint chain is preferred because it transfers torque rigidly and is easy to clean.

An alternate embodiment uses a wound wire flexible shaft between the two corner U-joints. The wire flexible shaft is assembled to the two corner U-joints with the hex fittings. While the wire flexible shaft has a lower cost, it is less preferred due to spring-like torque transfer (i.e. the shaft twists before torque is transmitted) and typical flexible shafts have cleanability problems.

While the drive train can be mounted externally on the curved body or internally in the curved body, it is preferred to mount the drive train internally for a number of reasons. The drive train rotates at high speeds in the reamer handle and there would be a risk to the surgeon if it were mounted externally. Additionally, it is possible for the drive train to catch on soft tissue if it is mounted externally. Also, external mounting increases the amount of instrument components in the surgeon's field of view, and consequently decreases the surgeon's view of the incision.

The drive train can be mounted permanently or it can be removable. The preferred embodiment is to have a removable drive train mounted internally. This allows for the drive train to be replaced as it wears out or becomes obsolete without replacing the entire instrument. In addition it allows the drive train to be removed for cleaning.

The drive train is captured inside the curved body through the use of the curved lid. The curved lid can be assembled and disassembled from the curved body so that the drive train can be removed for cleaning or replacement. The monoblock curved body and lid construction is preferred over a curved tube design. A solid curved tube with an internal drive train without a lid for access cannot easily be cleaned while a tube with a curved lid can be easily disassembled from the curved body so that the internal components like the U-joints and drive train can be easily cleaned. The curved lid adds strength to the curved body. The curved body and curved lid assembly can handle more axial load than an open curved body alone.

Modular holder/tips have been developed that mate with shell implants, polyethylene inserts and ceramic inserts. In the preferred embodiment, the modular tips all connect to the shell positioner/impactor in the same fashion. A spring-loaded button in the modular tip or holder deflects an internal ring to an aligned position and released after assembly to and then engages a groove on the shell positioner/impactor providing an axial capture. There are many different methods for achieving this type of connection between the modular holder and the shell positioner/impactor. A socket feature, such as in the modular tip engages a mating feature on the shell positioner/impactor providing a radial anti-rotation constraint. This allows torque to be transmitted between the curved body of the shell positioner/impactor and the modular tip body. In the preferred embody a hexagon or octagon is formed within the modular tip end. Obvious any shape which prevents radial and rotational movement can be used. Additionally in a preferred embodiment, an internal hex fitting in the modular tip engages a mating socket in the shell positioner/impactor. This allows for torque to be transmitted between the drive-train of the shell positioner/impactor to the hex fitting on the modular tip holder. Obviously the inverse of this design could also be used with the socket on the modular tip or holder.

In the preferred embodiment applying contrasting torque forces through the knob and handle of the shell positioner/impactor actuates and deactuates each modular holder/tip. A clockwise rotation of the knob results in a lock and counterclockwise rotation of the knob is used to unlock. The surgeon transmits torque internally through the instrument by turning the knob which then transmits torque to the drive-train to the hex fitting to the locking mechanism while external torque is transmitted from the surgeon to the handle to the curved body to the tip socket. These two contrasting forces allow for the actuation of the locking mechanisms from a distance. To transmit axial force the surgeon impacts the knob with a mallet which transfers force to the handle and the curved body then to the tip and finally to the implant.

In some incisions it would be preferred to introduce the shell and bearing insert without an instrument attached in order to reduce the overall cross-section of the assembly. This is challenging with a straight impactor for instance, because it is difficult to thread the straight impactor and shell together within the incision. Furthermore a straight impactor impinges on tissue making it even more difficult to align. The modular holder tip facilitates the coupling of the impactor/positioner with a cup by allowing the user to lock the holder/tip onto the implant prior to insertion, disconnect it from a shell positioner/impactor, insert the implant holder/tip assembly into the incision and reconnecting in vivo. This is because of the larger bore in the holder and the use of a quick connect feature. This method is particularly useful with the shell that can have a roughened surface that can catch on soft tissue upon insertion.

When the cup holder is designed to mate with shells with threaded drive holes a threaded stud is captured within the body of the cup holder/tip. The threaded stud can be rotated clockwise or counter-clockwise to thread onto or off of shell implants. A cup holder/tip could be designed to mate with other shell designs. Specifically, the cup tip could be modified to have an expanding collect that could engage a smooth bore feature in a shell. These cup tips would be similar to those discussed below for holding shell inserts.

Some shells have a cluster of screw holes that need to be positioned in a specific location in reference to the curved shell positioner/impactor. There are several methods for orienting the screw holes with a curved shell positioner/impactor. One method is to thread the shell on to the cup holder/tip and positioner/impactor assembly, disassemble the shell/cup holder combination from the shell positioner/impactor preferably by pressing a button, reorienting the shell with the screw holes in the correct orientation, and reconnecting the shell/cup holder to the shell positioner/impactor. Another method for orienting the screw holes requires the surgeon to thread the shell partially on to the cup tip. By holding the shell in the correct orientation in reference to the shell positioner/impactor, the surgeon can then lock the shell and cup holder together by rotating a knob.

Polyethylene insert holders are designed to mate with the bearing surface of a polyethylene bearing insert. In one typical design, a silicone ring is captured between four components: a hex fitting, a spherical head, a compression ring and a body. When the internal hex fitting is rotated clockwise the silicone ring is squeezed between the spherical head and the compression ring causing it to protrude and create a friction lock with the polyethylene insert. The friction lock allows the user to turn, push and pull the insert which facilitates the assembly of the polyethylene insert into the shell.

Ceramic insert holders are designed to mate with a titanium outer sleeve in which a ceramic bearing insert is typically mounted. A holder is provided in which a collet is captured between two components: a hex fitting and a body. When the internal hex fitting is rotated clockwise the collet is expanded and creates a friction lock with the titanium sleeve of the ceramic insert. The friction lock allows the user to turn, push and pull the ceramic insert that facilitates the assembly of the ceramic insert into the shell.

Modular alignment guides have been developed that mate with the reamer handle and shell positioner/impactor. The modular alignment guides have a mechanism that allows the user to easily connect/disconnect the alignment guides from the acetabular instrument and to index the alignment guide around the axis of the instrument into the preferred position. It is preferred to be able to switch between a mechanical and navigation-based alignment guide. A navigation guide typically has a tracker with light emitting diodes that can be tracked via an optical system in the operating room. This allows the user to determine which method of alignment will be used and assemble the necessary guide. This in turn decreases the number of instruments in surgery.

In the preferred alignment guide embodiment, the mechanism is actuated by pressing a button that forces the translation of a locking pin perpendicular to the translation of the button. With the button pressed, the user can assemble the alignment guide to the guide fixture over the machined flats of the guide fixture. After passing the flats, the alignment guide can be rotated around the guide fixture to the preferred location. Once the preferred location is reached, the button is released and a lock pin engages the mating feature such as a bore in the guide fixture. The lock pin is spring-loaded into that position. In order to remove the alignment guide the operations are reversed.

Currently alignment guides designed for curved acetabular instruments are positioned in the same plane as the curve of the curved body. It is preferred to be able to position alignment guide independent of the curved body. The curved body should first be positioned to minimize impingement and then the alignment guides can be positioned to optimize their functionality. For a mechanical alignment guide this would involve positioning it so that it is perpendicular to the floor or patient. For a navigation-based alignment guide the user would position it to maximize visibility to the navigation cameras and to optimize the weight distribution of the navigation tracker.

While in the preferred system a separate reamer handle and a positioner/impactor is provided, it may be desirable to combine the two instruments into one instrument. This might be preferred because it would reduce the number of instruments in surgery and reduce the cost and weight of instruments. This may be accomplished through the use of modular attachments on either end of a curved body. A modular reamer locking mechanism is provided that attaches to the curved body in similar fashion to the modular holders. The main difference is that the modular reamer holder would not have a contrasting torque force supplied by the curved body. The modular reamer holder rotates freely around the curved body when torque is applied internally through the drive train. A modular impact handle can also be provided that connects with the same fitting that the power reamer attaches. The locking mechanism could be similar to those used in the modular holders. This modular impact handle would apply torque internally from a knob to the drive fitting then to the drive train of the curved instrument and would apply torque externally from the handle itself to the curved body. Axial forces would be translated from the knob to the handle to the curved body.

BRIEF DESCRIPTION OF DRAWINGS

FIG. 8 is an isometric view of the acetabular instrument of FIG. 1 and viewed from the holder end;

FIG. 9 is an enlarged view of the circle area of FIG. 8 showing a female hex socket for receiving a coupling element which releasably couples to a modulator holder tip which may engage an acetabular cup shell or reaming instrument;

FIG. 16 is an isometric view of the acetabular instrument of FIG. 1 showing the spring biased door release mechanism of the present invention;

FIG. 17 is an enlarged view of the circled area of FIG. 16;

DETAILED DESCRIPTION

Figure 1:
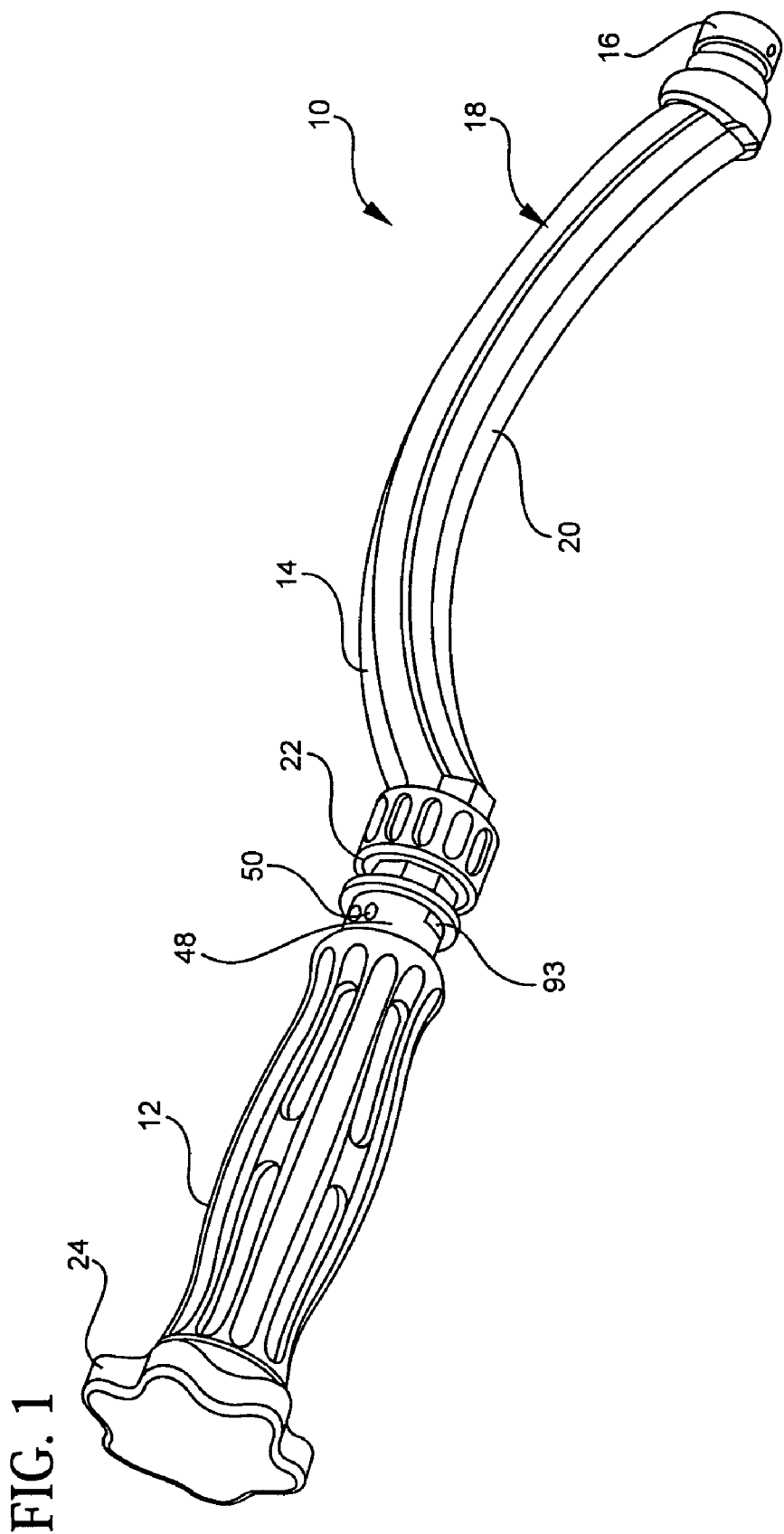
FIG. 1 is an isometric view of the acetabular instrument of the present invention, including a handle portion and a curved shaft portion and an instrument holder.
Figure 2:
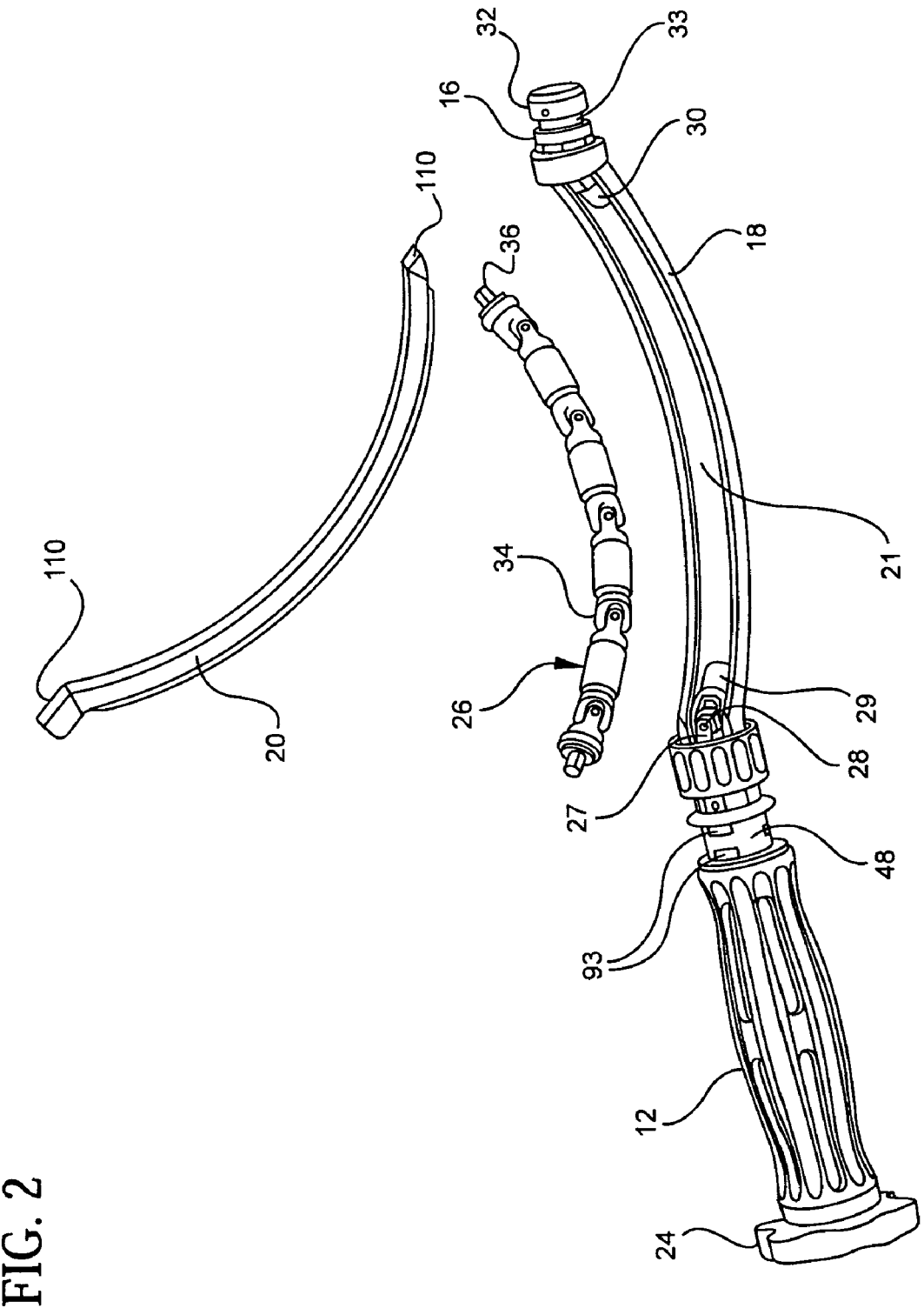
FIG. 2 is a partial disassembled view of the acetabular instrument of FIG. 1 showing the removable, flexible drive shaft and a removable lid portion which allows access to the interior of the hollow body of the curved portion.

Referring to FIG. 1 there is shown the acetabular instrument of the present invention generally denoted as 10. The instrument has a handle portion 12, a hollow non-linear preferably curved body portion 14 and an instrument holder portion 16. In the preferred embodiment, curved hollow body portion 14 has a body portion 18 and a lid 20 which are machined from a single solid piece of metal, such as stainless steel. Other suitable materials could be used. Main body portion 18 and lid 20 surround a hollow internal portion 21 as shown in FIG. 2. The removable lid portion 20 is releasable via a spring-loaded release sleeve 22. A rotatable knob 24 is mounted at one end of handle 12 and is attached to a solid shaft extending through handle portion 14 to a u-joint drive element 28. U-joint drive element 28 has a portion 27 fixedly coupled to the shaft on knob 24 and a portion 29 extending into the interior 21 of curved portion 14.

Figure 3:
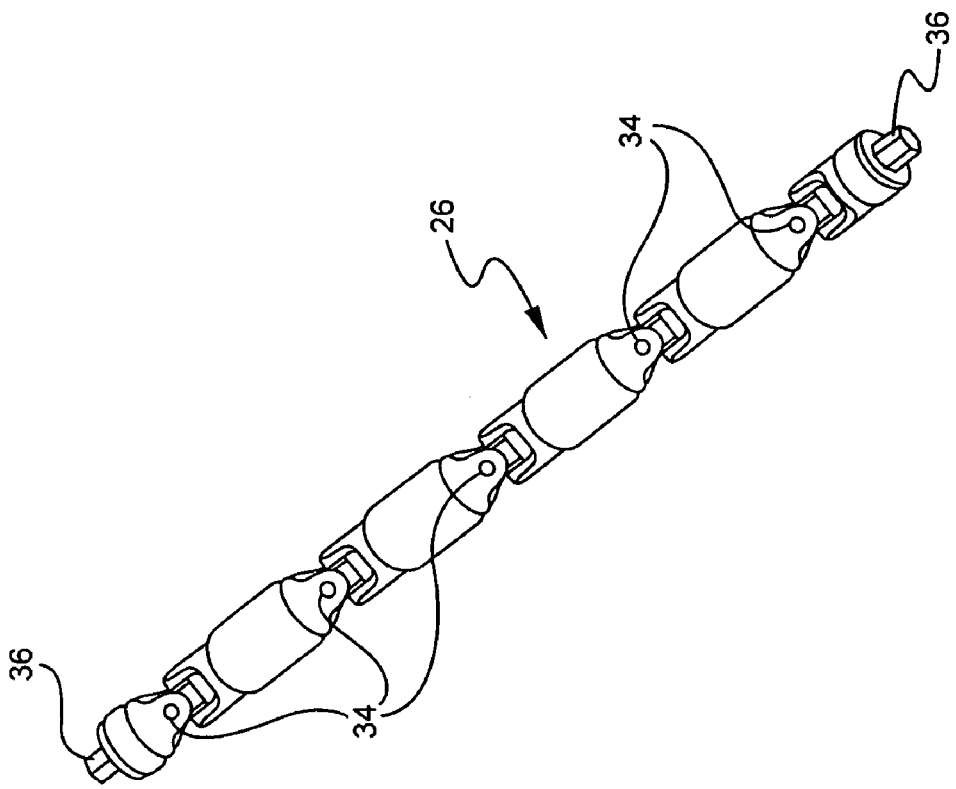
FIG. 3 is an isometric view of the flexible drive shaft shown in FIG. 2 comprising a series of U-joints shown in a coaxially aligned orientation.

Referring to FIGS. 2 and 3, there is shown an exploded view of the acetabular instrument 10 of FIG. 1 in which curved lid 20 is shown removed from curved body portion 18. In addition, a flexible shaft portion 26 is shown removed from the interior 21 of hollow portion 14. It can be seen from FIGS. 2, 4, and 5 that the ends of body portion 18 include U-joint elements 28 and 30 respectively. U-joint 30 includes a portion 31 connected to holder 16 and an inner portion 39 extending into hollow portion 21 of curved portion 14. The inner ends 29, 39 of U-joint portions 28 and 30 are connected to, in the preferred embodiment, a solid drive shaft in handle 12 and a hex socket 70 of FIG. 9 within holder 16. The drive shaft within handle 12 is fixed to knob 24 so that rotation knob 24 rotates the drive shift and the U-joint 28. Rotation of the U-joint 30 causes a rotation of inner hex socket 70 of holder 16.

As best seen in FIG. 3, the rotatable drive shaft 26 includes a series of at least two and preferably five standard U-joints 34. Both ends of the flexible drive shaft 26 include male hex drives 36 which are received in mating hex sockets in both U-joint 28 and 30. Socket 40 is shown in U-joint 30 and a socket 41 is shown in U-joint 28 (see FIG. 17A) which has an identical socket. While five U-joints are shown in preferred flexible shaft 26, more or fewer could be utilized depending on the length of curved portion 14. Additionally, it is possible to use other types of flexible drive shafts known in the art with each preferably having a pair of hex drives 36 at their ends to make them removable from the curved portion 14.

Figure 5:
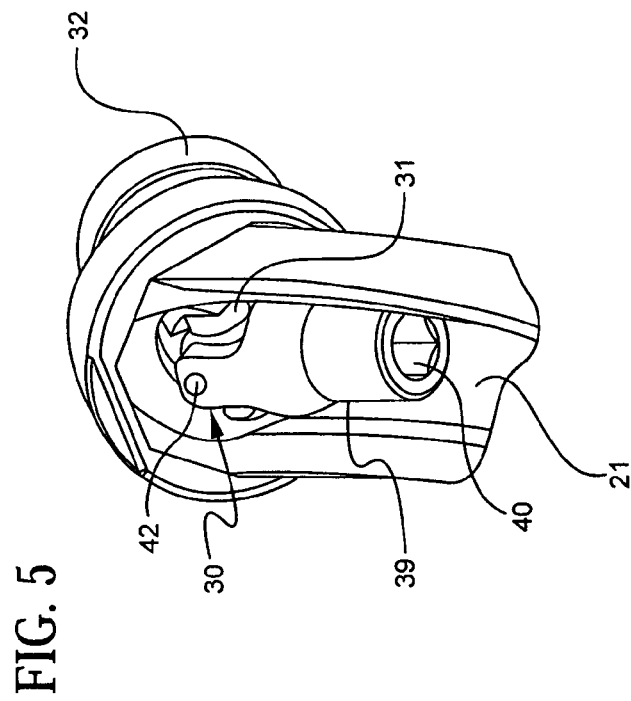
FIG. 5 is an enlarged view of the circle area of FIG. 4.
Figure 4:
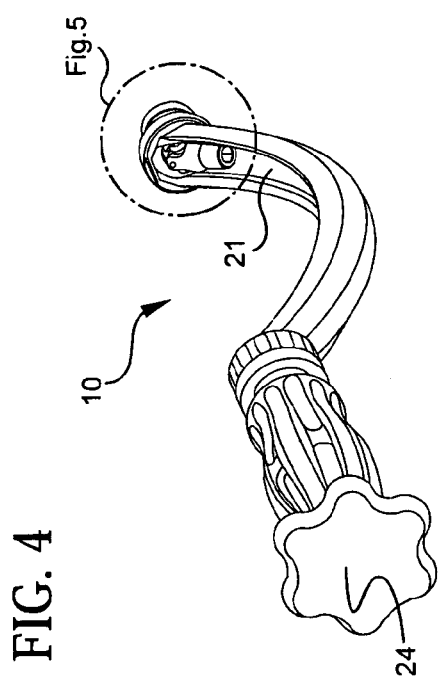
FIG. 4 is an isometric view of the acetabular instrument of FIG. 1 from the handle end with the lid removed showing a U-joint drive portion fixed to the instrument holder portion.

Referring to FIGS. 4 and 5, there is shown an isometric view of acetabular instrument 10 when viewed from the end having knob 24. When viewed from this angle, the U-joint 30 can be seen which includes the female hex socket 40. U-joint 30 is a typical U-joint having a pair of pivot pins with a pivot pin 42 shown in FIG. 5. As discussed above, flexible U-joint shaft 26 may be coupled at one end to socket 29 and at the other to socket 39 of U-joint 30 so that rotation of the flexible shaft causes rotation of inner hex socket 70 of holder 16. Note that in both FIGS. 4 and 5, lid 20 has been removed and is not shown.

Figure 6:
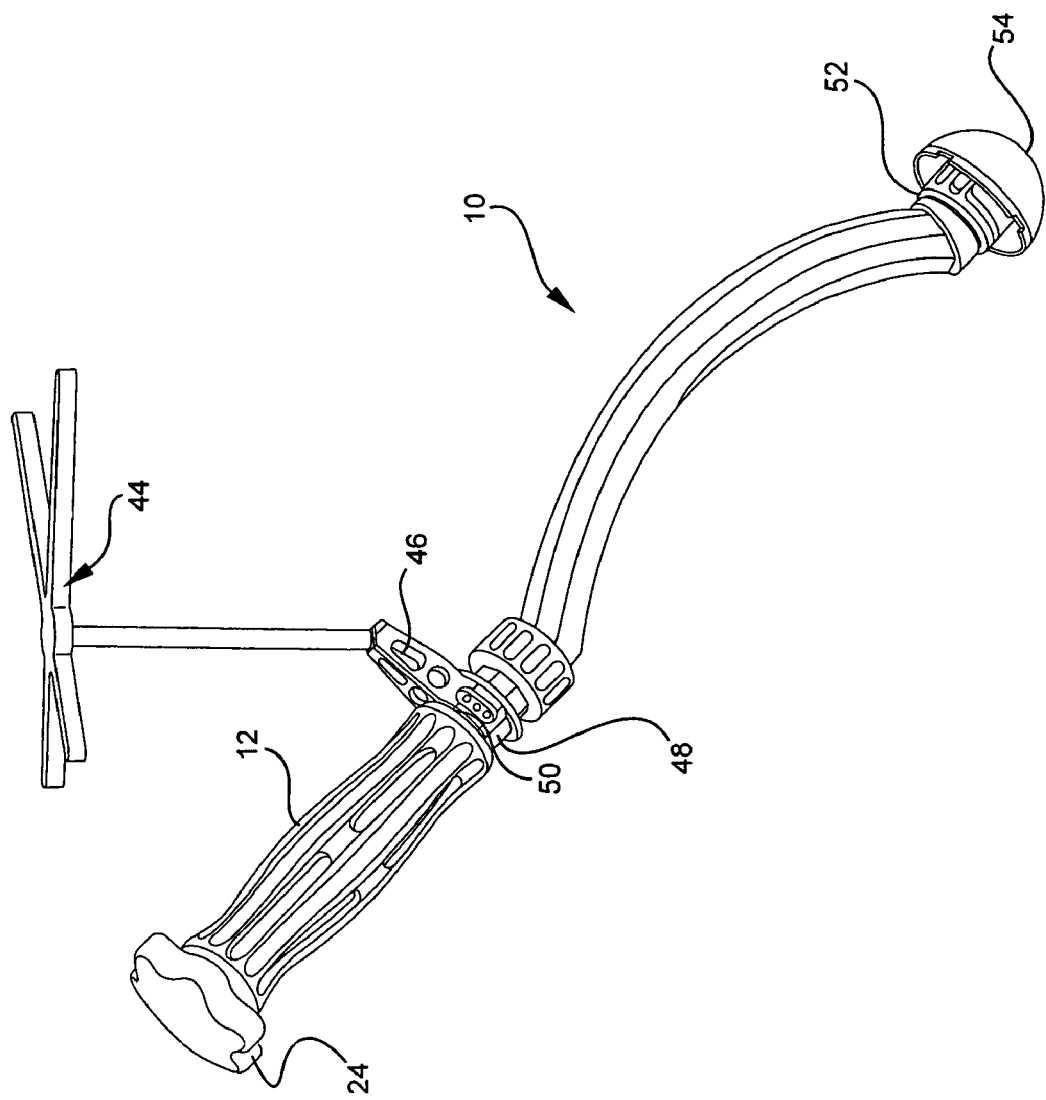
FIG. 6 is an isometric view of the acetabular instrument shown in FIG. 1 with an acetabular cup outer shell mounted on the holder and including an alignment instrument clipped on or adjacent the handle of the instrument.

Referring to FIG. 6 there is shown the acetabular instrument of FIG. 1 including a removable alignment guide 44, which includes a releasable attachment mechanism shown generally at 46, which can be attached to a portion 48 of instrument 10, which, in the preferred embodiment, is immediately adjacent handle 12. Releasable attachment mechanism 46 is shown in greater detail in FIG. 19. In the preferred embodiment, area 48 includes a plurality of recesses 50, which serve to locate gripping portion 46 of guide 44 in an indexable fashion. Surface 48 also has a pair of diametrically opposed flats for attaching modular alignment guide 44. Thus, the alignment device 44 can be indexed around surface 48 with respect to the orientation of curved portion 14. Also shown in FIG. 6 is a coupling element 52, which can be mounted on tip portion 32 for rotation therewith of holder 16. Such coupling elements are known and releasably couple an acetabular reamer or shell 54 thereto for rotation therewith. Thus, coupling element or holder 52 is coupled to tip portion 32 for rotation in conjunction with internal hex socket 70. Preferably the coupling is a quick release type coupling which utilize groove 33 and a spring loaded locking element to form an automatic coupling as will be discussed in more detail below. Alternately, if knob 24 is used as an impaction surface, force is delivered thereto, as by a mallet, and transferred through the rigid body portion 14 to holder 16 and then into, for example, a press fit shell 54.

Figure 7:
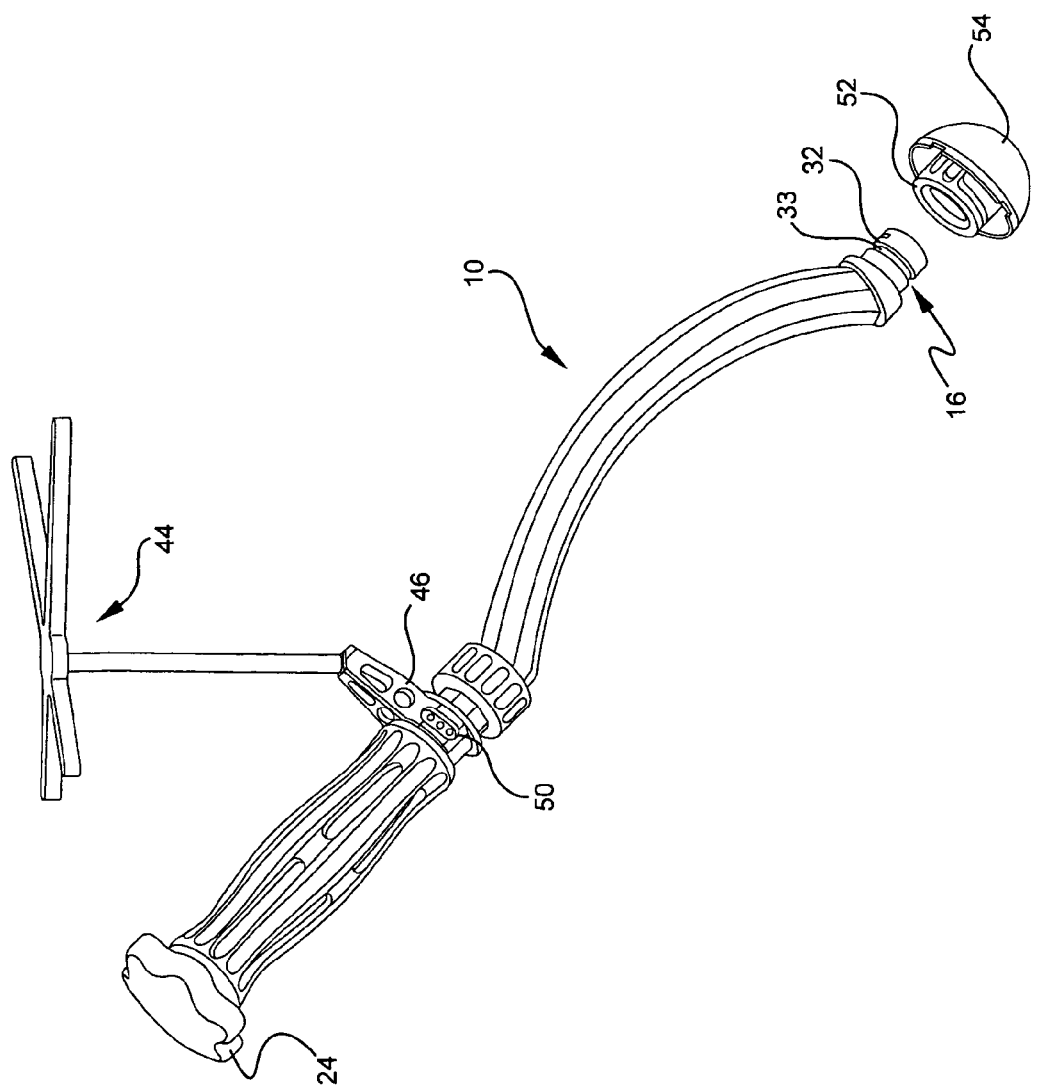
FIG. 7 is an isometric view of the acetabular instrument of FIG. 6 showing the acetabular shell with the acetabular shell including a modular holder/tip releasably coupled thereto disassembled from the acetabular instrument.

Referring to FIG. 7, there is shown the coupling element 52 and shell 54 detached from holder 16 of instrument 10, also shown is alignment element 44, as shown in FIG. 6.

Referring to FIGS. 8 and 9, there is an isometric view of instrument 10 from holder end 16 with FIG. 9 showing an enlarged view of holder 16. In the preferred embodiment, portion 32 of holder 16 includes a female hex socket 70 for receiving a male hex drive on the coupling element such as 82, 82' and 82" shown in FIGS. 10, 12 and 15. In the preferred embodiment enlarged portion 32 rotates along with polygonal plate 72, which plate includes peaks 74 adapted to engage recesses in coupling element 52 as will be described hereinbelow.

Figure 11:
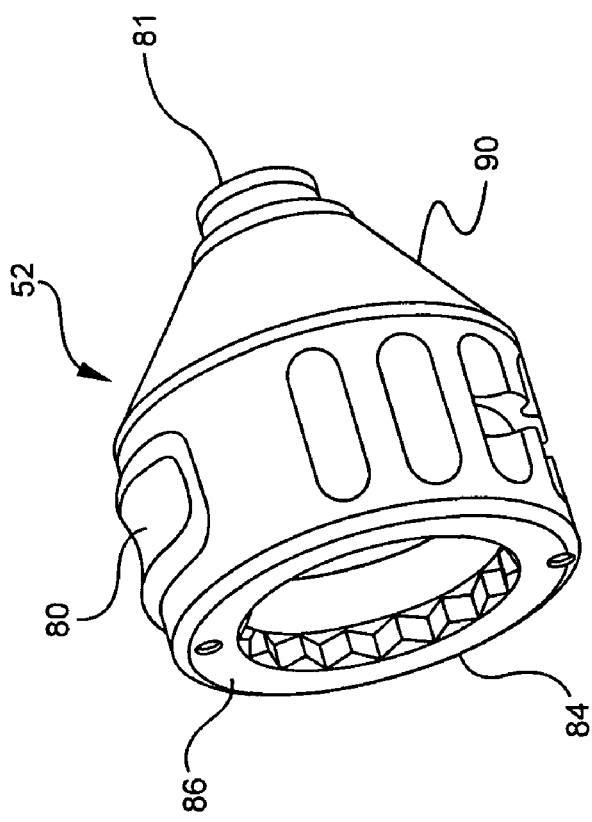
FIGS. 10 and 11 are typical coupling elements or holders which couple to the female hex socket of FIG. 9 and which releasably engage an acetabular shell.
Figure 10:
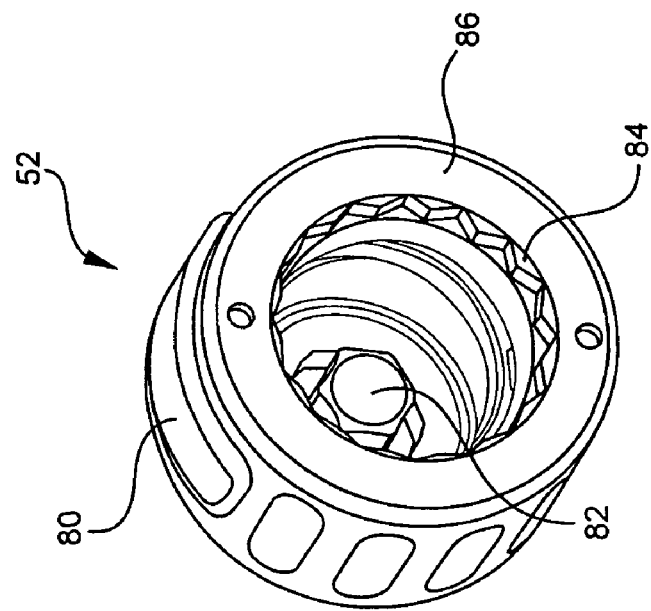

Referring to FIGS. 10 and 11, there is shown one embodiment of a coupling element 52, which includes a threaded tip 81 for engaging a threaded bore in a shell. The tip 81 is housed within a tapered portion 90. In addition, FIG. 10 shows the male hex 82, which is received within the bore 70 of holder 16. Male hex 82 is directly connected to thread 81. In addition, a plurality of circumferential teeth 84 are positioned around the end 86 of coupling element 52 to engage mating teeth 74 of holder 16 to ensure no relative rotation occurs between the holder and the handle when the drive shaft is rotated. A Button 80 acts as a quick connect/release actuator which moves a locking element into and out of engagement with the end of curved shaft portion to release all of the holders/tips shown in FIGS. 11-15.

Figure 13:
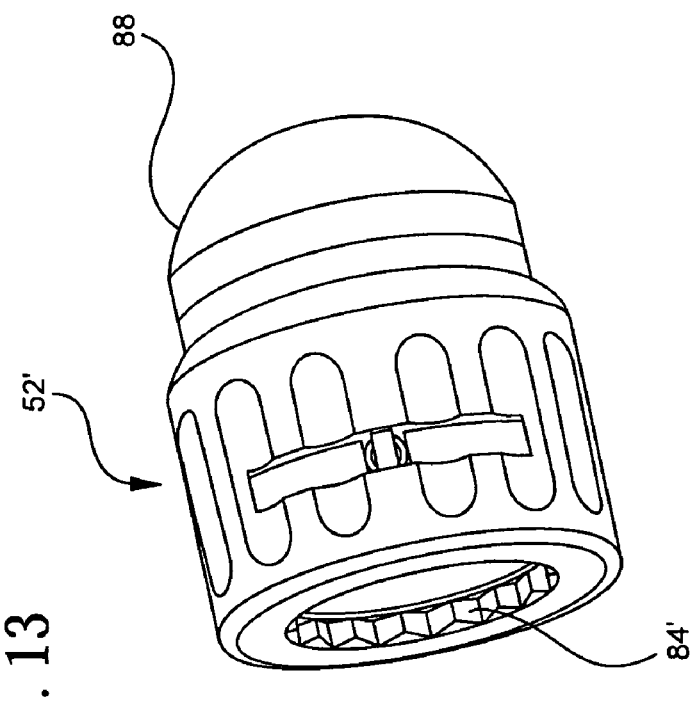
FIGS. 12 and 13 are isometric views of a second embodiment for a coupling element or holder adapted to engage a polyethylene bearing insert for an acetabular cup.
Figure 12:
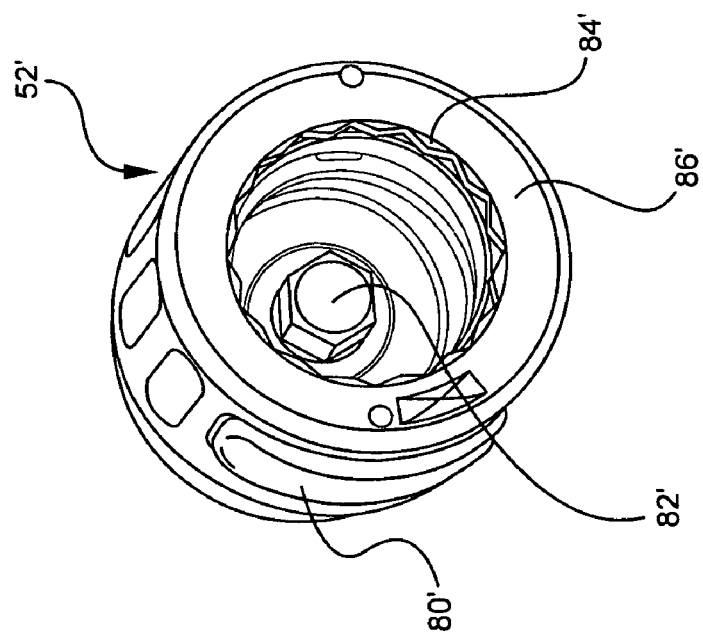

Referring to FIGS. 12 and 13, there is an alternate embodiment of the holder 52' which is used to engage a polyethylene bearing insert and impact the same into acetabular shell 54. This holder has a dome-shaped surface 88 whereas the coupling element of FIG. 11 has a threaded tip 81. Otherwise, the coupling elements of FIGS. 12 and 13 have similar structural coupling features as the coupling element of FIGS. 10 and 11 and have been numbered correspondingly.

Figure 15:
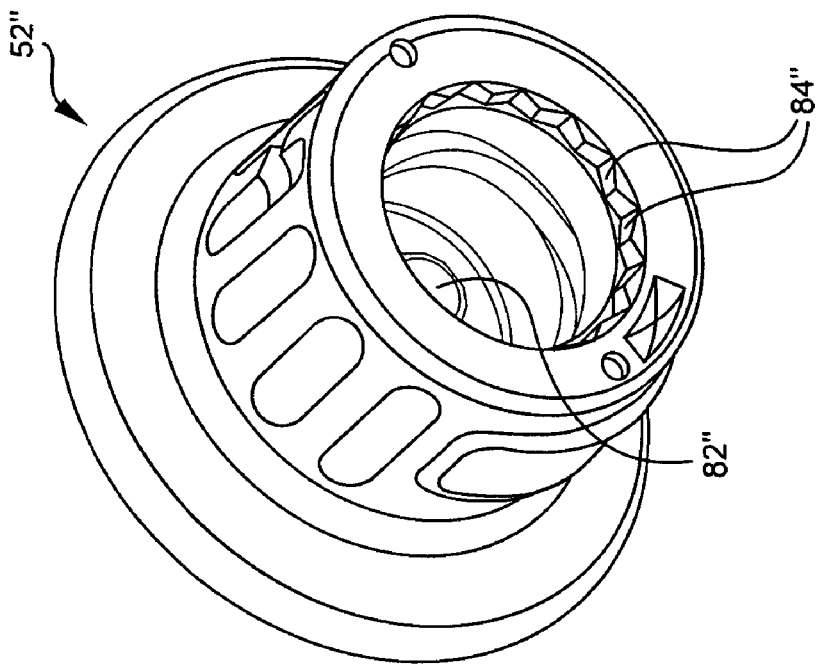
FIGS. 14 and 15 are yet another embodiment of a coupling or holder adapted to engage a metal sleeve housing a ceramic acetabular shell or reamer.
Figure 14:
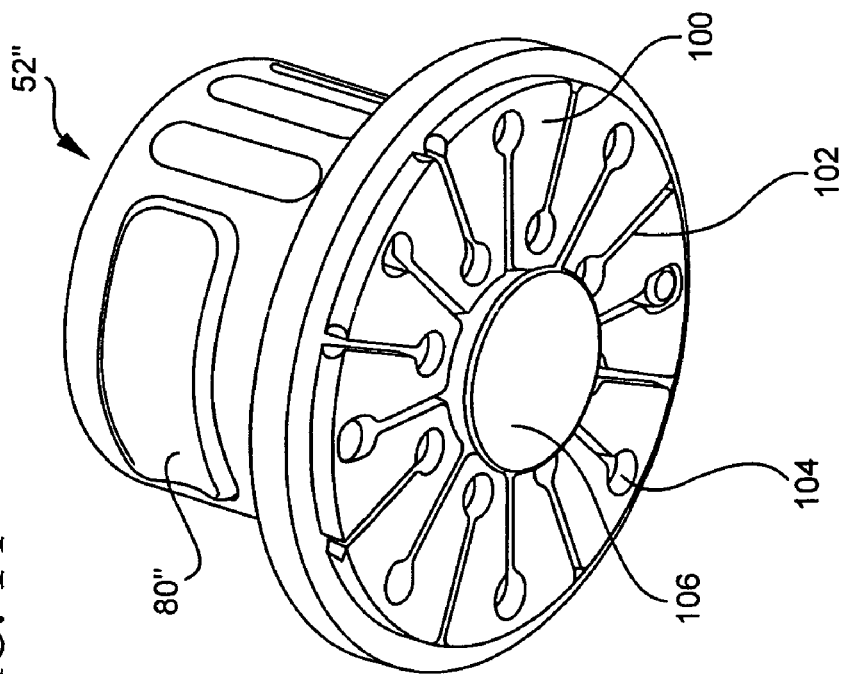
Figure 15A:
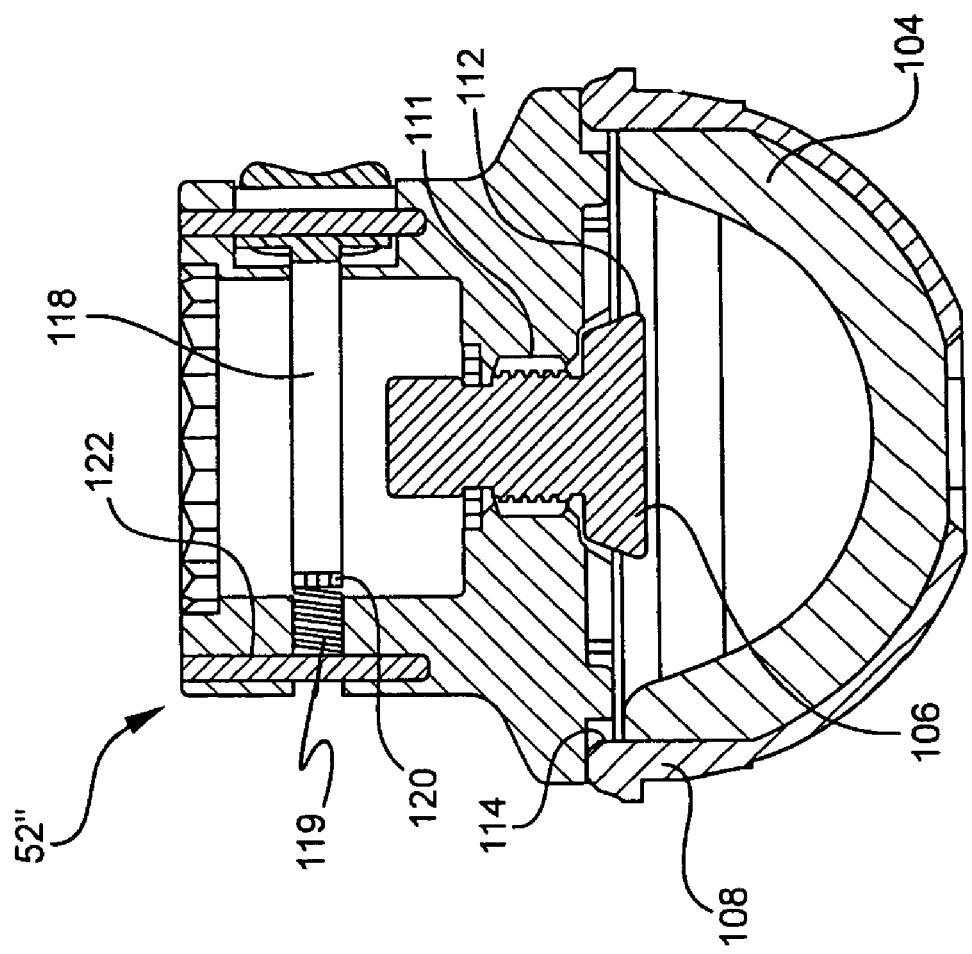
FIG. 15A is a cross-sectional view of the holder of FIGS. 14 and 15 with a ceramic bearing mounted in a metal sleeve coupled thereto.

Referring to FIGS. 14 and 15 there is shown yet a third embodiment of a coupling element 52" which includes a serrated plate or expansion collet 100 adapted to grip the inner perimeter a ceramic bearing mounted in a metal sleeve as shown in FIG. 15A. A slotted expansion collet 100 includes a plurality of slits 102 preferably ending in expanded portions 104. The slits 104 allow the plate to be slightly radially expanded by movement of actuating cone 106 to thereby lock to an inner diameter of a ceramic insert sleeve 54. Again, the coupling portion of the element 52' is similar to those previously described in that it has a male hex drive 82" and a serrated circumference 84".

FIG. 15A is a cross-sectional view of holder 52" with collet 100. Collet 100 is expanded by the movement of tapered end portion 106 of male hex drive 82". As can be seen from FIG. 15A holder 52" has a central threaded bore 111 so that rotation of the male hex 82" causes tapered portion 106 to move with respect to collet 100. When moved axially toward the instrument, tapered surface 112 engages the central bore of collet 100 and causes the outer diameter of collet 100 to expand slightly due to a slight increase in the width of slots 102. This causes the outer periphery of collet 100 to tightly engage the inner surface 114 of metal sleeve 108. Also shown in FIG. 15A is release button 80" including a shaft 118 which acts against spacing 119 to move quick release element 120 out of bore 122 of holder 52". Element 120 automatically compresses spring 119 when the tip 32 of the instrument 101 is moved into bore 122. Element 120 snaps back into a groove or recess 33 in tip 32 to couple the holder to the instrument. Depression of button 80" allows the two parts to be disassembled.

Figure 17A:
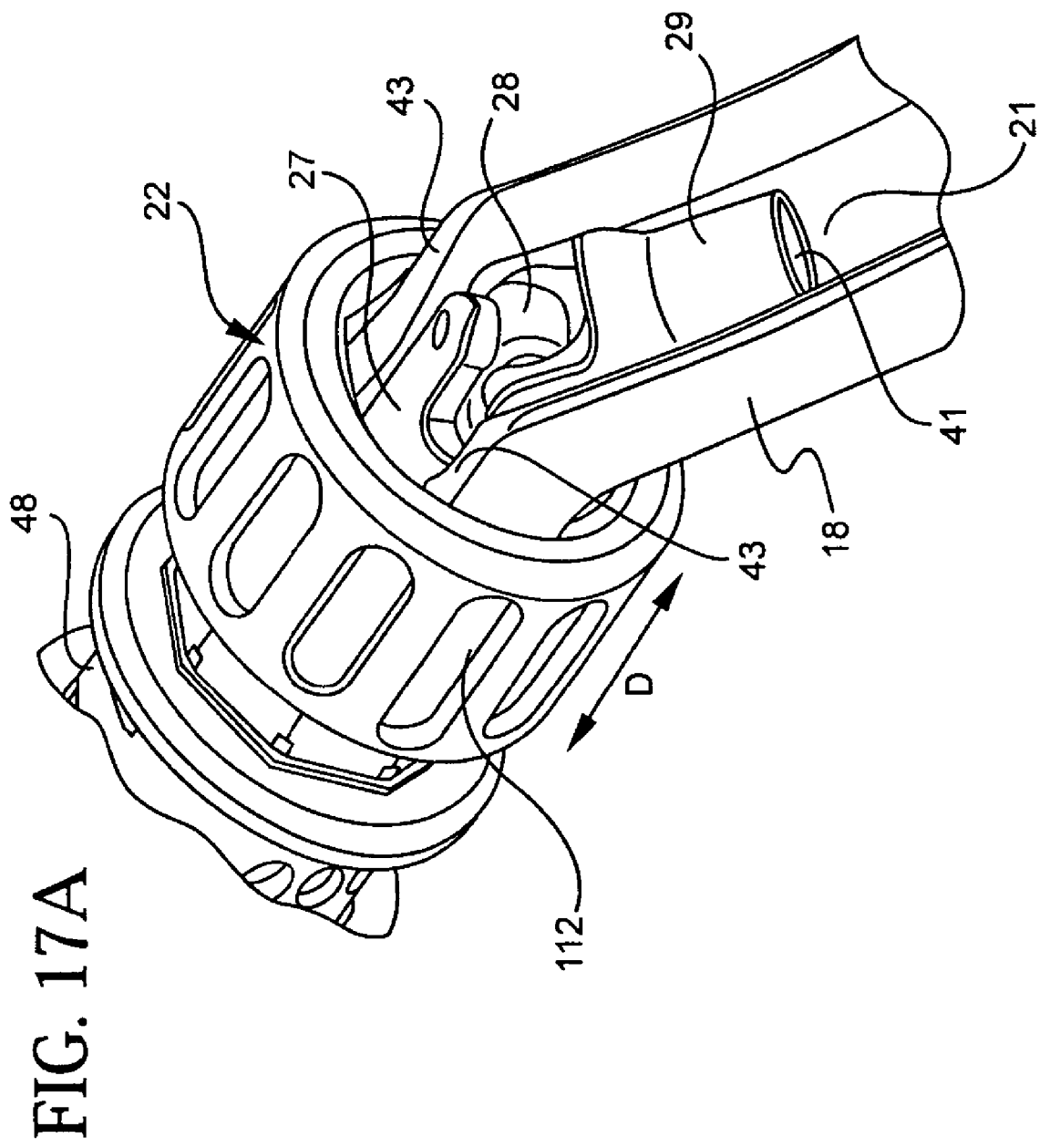
FIG. 17A is an enlarged view of the circled area of FIG. 16 showing the U-joint at the handle end and the tongue and groove coupling system for the lid.

Referring to FIGS. 16, 17 and 17A, there is shown the release mechanism for curved lid 20 of offset or curved portion 18. In the preferred embodiment lid 20 has a tongue portion 110 at each end, which can be slid into a groove in the opening of holder 16 and then into a groove formed in the handle end of body 18 and finally locked in position by spring biased locking element 22. To insert or release lid 20, locking element 22 is moved against the force of a spring 112 toward the left-hand side of FIG. 17 to allow portion 110 to be moved away from the adjacent portion of body 18 of curved portion 14. When lid 20 is assembled by first placing end 110 into holder 16, the lid is closed by inserting the tongue into the groove adjacent the handle and releasing locking element 22 to hold the door in position after the flexible shaft 26 has been inserted.

FIG. 17A is an enlarged isometric view of the circled detail of FIG. 17. This view shows U-joint 28 with end 27 coupled to the shaft going through handle 12. The end 29 includes female socket 41. Also shown are surfaces 43 on which ends 110 of lid 20 rest when the lid is assembled to body 18. Sleeve 22 moves in the direction of the arrows "D" to either lock or release lid 20.

Figure 18:
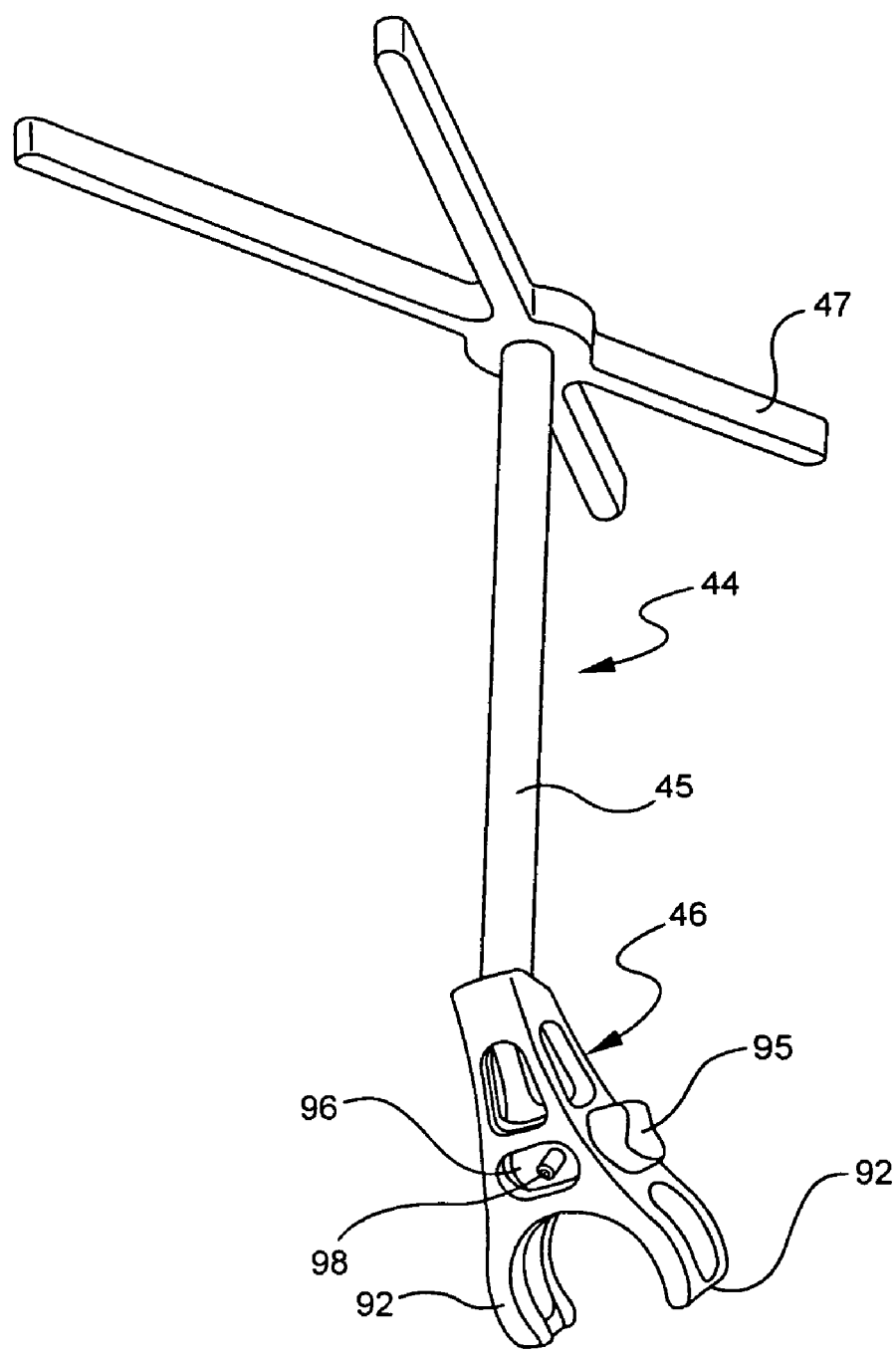
FIG. 18 is an isometric view of the alignment device which is releasably attachable to the acetabular instrument as is shown in FIG. 7.
Figure 19:
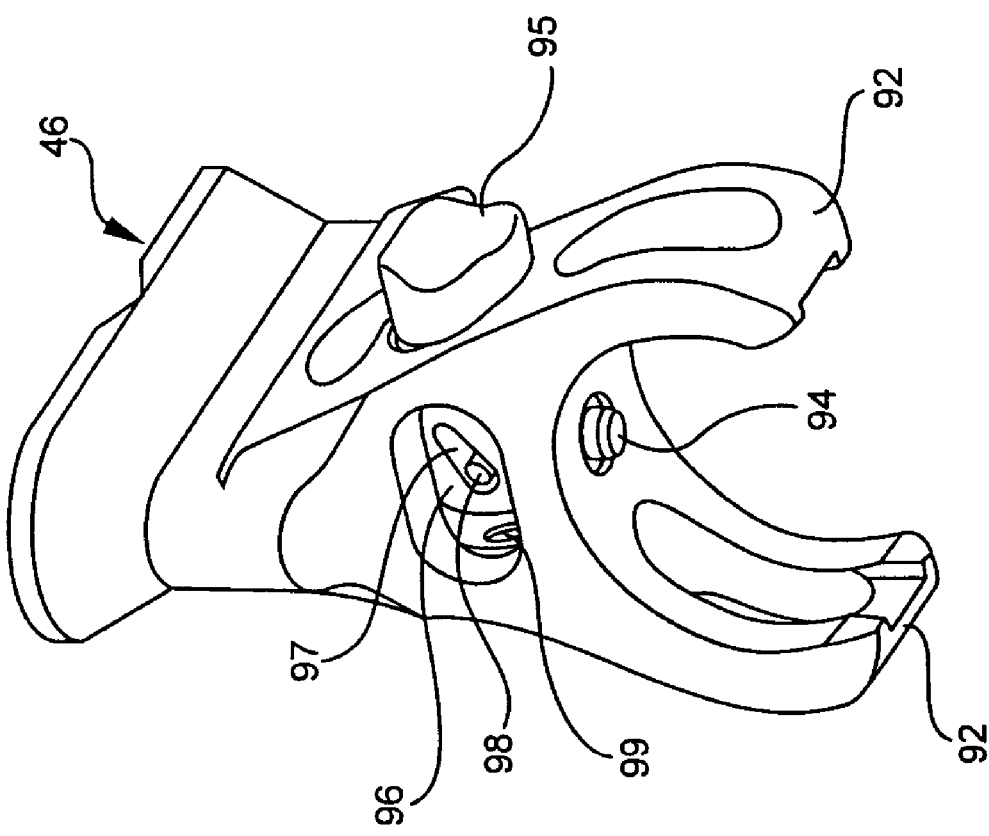
FIG. 19 is a enlarged view of the modular alignment guide attachment element of FIG. 18.

Referring to FIG. 18, there is shown releasable alignment element 44, which has gripping portion 46, which couples to portion 48 as shown best in FIGS. 17 and 17A. As is shown in FIGS. 17 and 17A there are a plurality of indexing positions in which alignment element 44 can be placed. A pin 94, shown in FIG. 19 is located within attachment portion 46 and engages a particular indexing bore or recesses 50 to hold the alignment element in the proper orientation with respect to curve shaft portion 14. While a tongue and groove is used in the preferred embodiment, a lid having a hinge connection at one end could be utilized.

Referring to FIGS. 18 and 19, the alignment device 44 includes a shaft 45 coupling alignment elements 47 to gripping portion 46. Portion 46 is shown detached from shaft 45 and enlarged in FIG. 19 and has a pair of arms 92 which, during assembly, engage flats 93 on portion 48 of instrument 10 as shown in FIGS. 1 and 2. When fully inserted, the ends of arms 92 extend beyond slots 94 to allow rotation of device 44. Preferably there are four flats with two spaced flats in diametrically opposed sides of area 48. A pin 94 is biased downwardly towards arm 92 which can snap into bores 50 on portion 48. A spring loaded release button 95 has a shaft 96 with a cam slot 97 therein coupled to pin 94 by cam follower 98. Shaft 96, and therefore cam follower 98, are biased by a spring 99 to a position where pin 94 is extended. Because slot 97 is angled with respect to the axis of pin 94 depression of button 95 moves shaft 96 against the force of spring 99 (to the left in FIG. 19) thereby withdrawing pin 94 from its engagement with bore 50. This allows the alignment device 44 to be rotated around area 48 as desired to place alignment elements 47 in the proper position. This system may also be used to attach an optical tracker used in computer navigation to the positioner/impacter/reamer handle.

Figure 20:
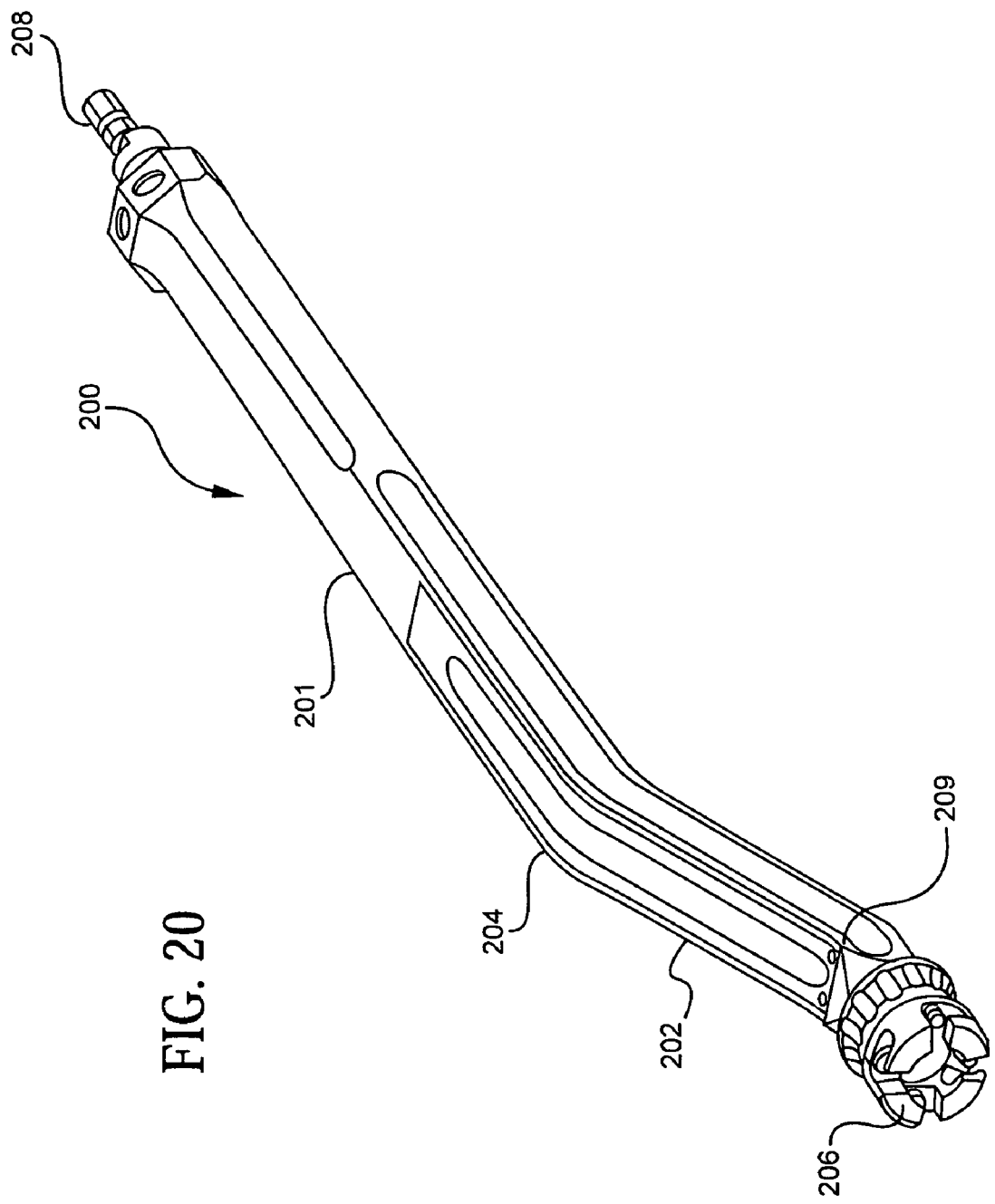
FIG. 20 is an isometric view of a curved offset reamer handle with a removable lid assembly.

While the curved portion 14 is curved in-line it could just as well be bent to form an offset portion as shown in several prior art publications. As shown in FIG. 20 the preferred offset curved instrument 200 has a pair of straight sections 201, 202 joined by two curved sections 204 and 209 to produce an instrument, which while not having a long arcuate section, can still avoid impingement with soft tissues. Instrument 200 is designed as a reamer with a reamer attachment head 206 mounted at the leading end and a input for rotary motion 208 at the other end. Attachment head 206 is similar to that shown in U.S. Pat. No. 5,658,290.

Figure 21:
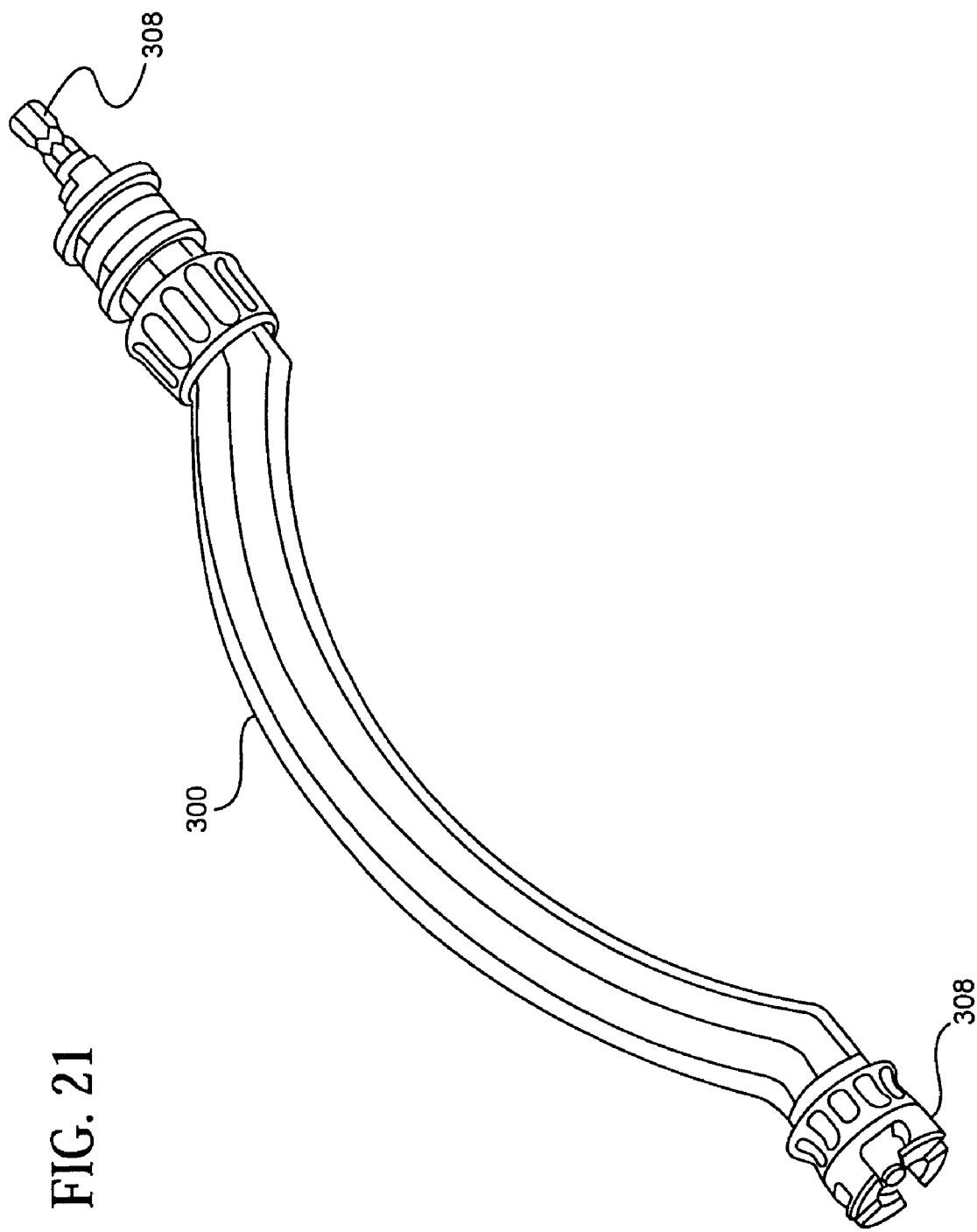
FIG. 21 is an isometric view of a curved inline reamer handle with a removable lid assembly.
Figure 22:
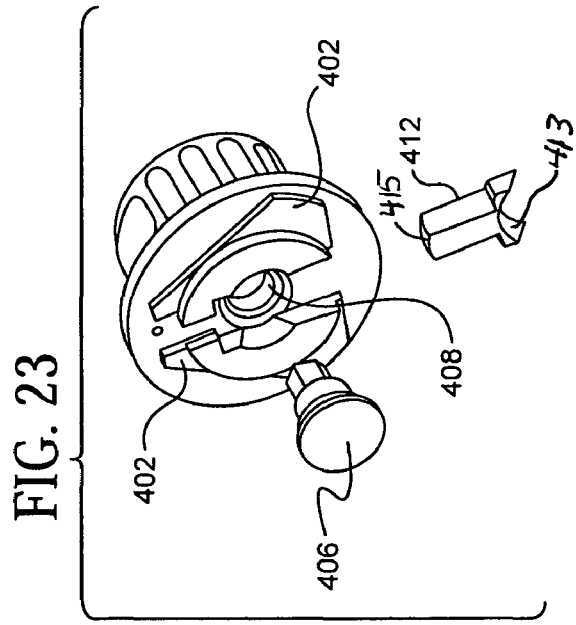
FIG. 22 is an isometric view of still another embodiment of a coupling element or holder adapted to engage a ceramic bearing element mounted in a metal sleeve.
Figure 23:
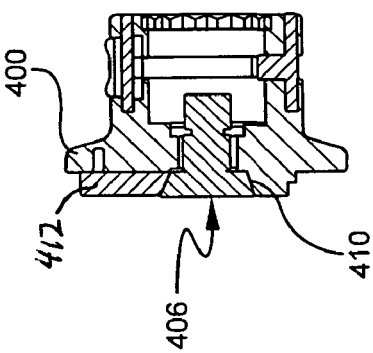
FIG. 23 is a partial exploded isometric view of the holder of FIG. 22.
Figure 24:
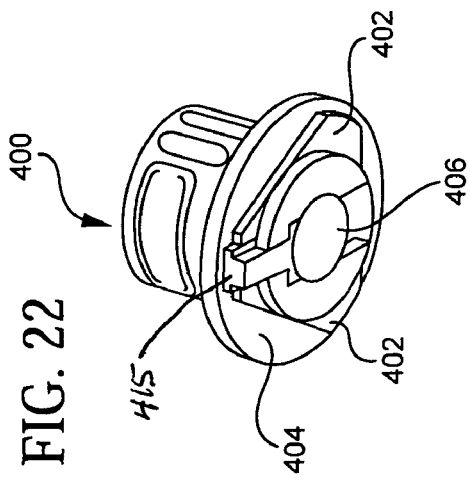
FIG. 24 is an end view of the holder of FIG. 22.
Figure 25:
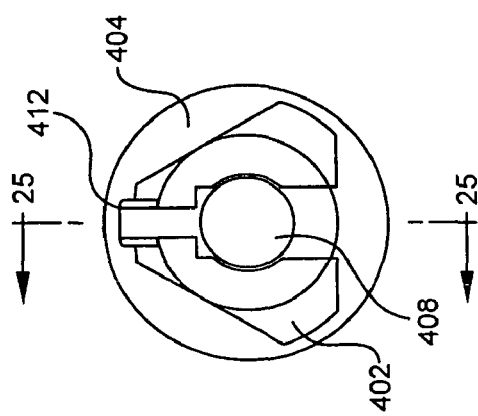
FIG. 25 is a cross-sectional view of the holder of FIG. 22 along lines 25-25 of FIG. 24.
Figure 26:
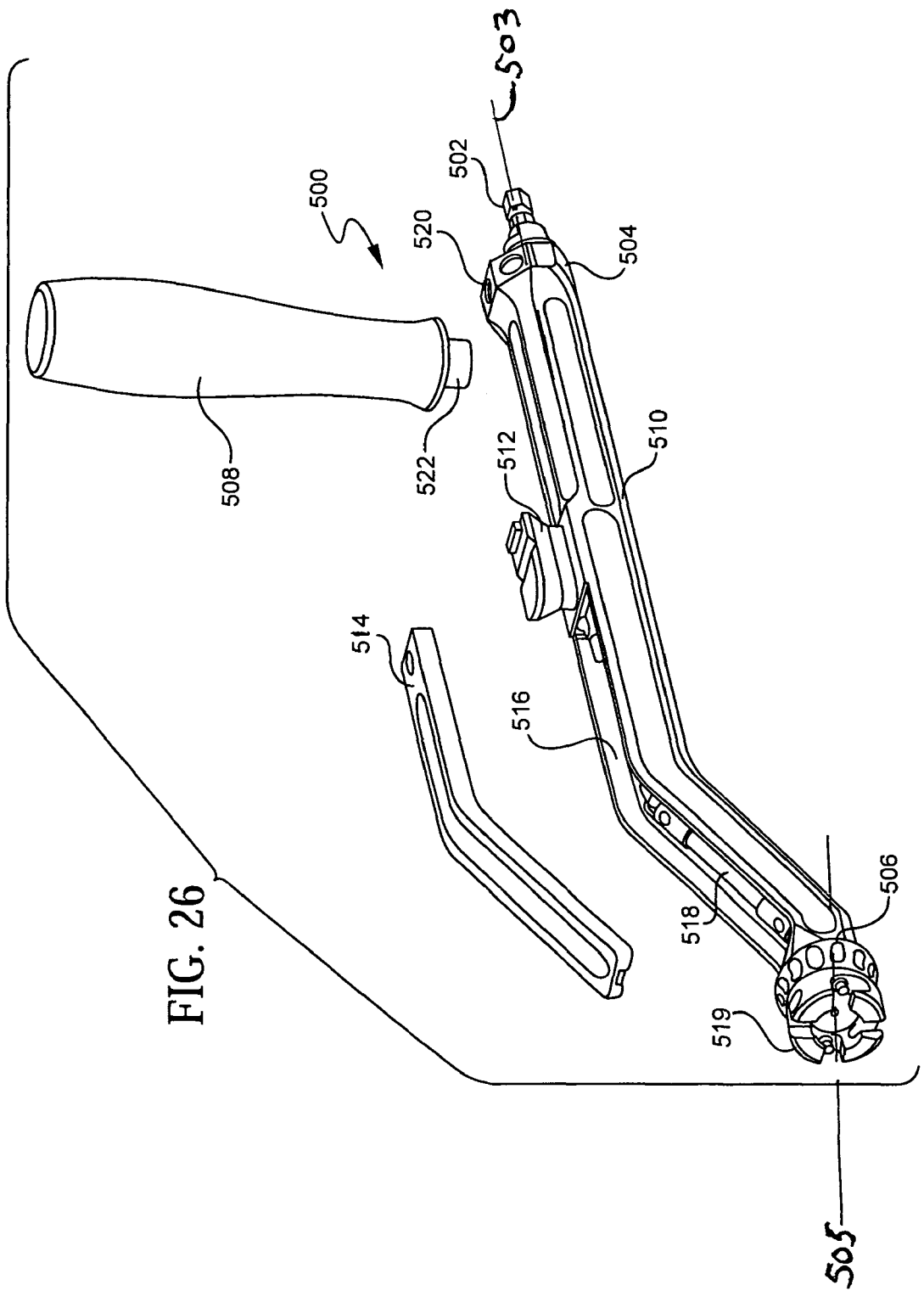
FIG. 26 is an exploded view of an offset reaming handle including a reamer attachment head at the leading end thereof in the drive at the trailing end thereof.

FIG. 21 shows a curved inline instrument 300 in the form of a reamer having drive end 308 and a reamer head attachment end 306 identical to those shown in FIG. 20. The internal drive system is also identical to that described for curved instrument 10.

Referring to FIGS. 22-25 there is shown still an alternate holder embodiment generally noted as 400. Holder 400 includes a pair of radially extending arms 402 which are fixedly mounted on a base plate 404. A slidable locking element 412 is spring-biased toward the center of base plate 404 and has an end 413 which intersects a central threaded bore 408 in holder 400. Locking element 412 slides in a track formed between arms 402 and has an end 415 which contact the acetabular cup. A threaded actuation element 406 engages threaded bore 408 in plate 404. Actuation element 406 includes a tapered surface 410 best seen in FIG. 25 which engages a tapered surface on end 413 of locking element 412 to initiate the radially outward sliding movement. A quick release system identical to that shown in FIG. 15A is utilized to attach the holder to the leading end of an impactor as shown in FIGS. 34-37. While alternate holder 400 is similar in operation to holder 100 shown in FIG. 14-15A, it is simpler to manufacture and thereby less costly.

Figure 27:
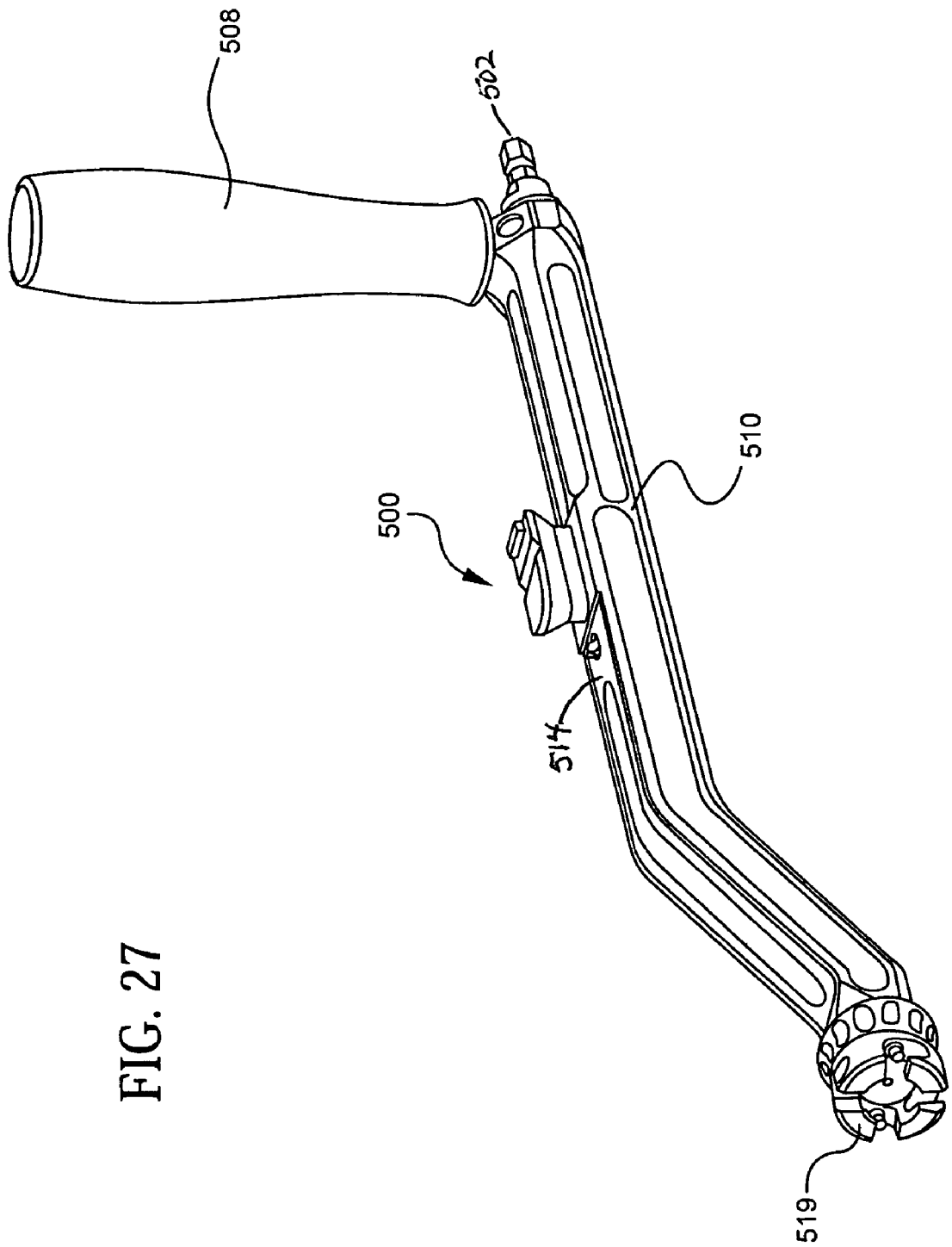
FIG. 27 is an assembled view of the reamer handle of FIG. 26.

Referring to FIGS. 26-33, there is shown an alternate embodiment of a reaming handle generally denoted as 500. Reaming handle 500 is offset in that an axis 503 of drive element 502 at trailing end 504 is offset from the axis 505 of the leading end 506. Reamer handle 500 includes a hand grip 508 which is releasably attachable to a body 510 of handle 500. Integral with body 510 is a navigation coupling element anchoring boss 512 which is capable of receiving either a mechanical alignment element or an optical tracker element for use with a computer-aided navigation system. A removable cover 514 is attached to body 510 over a drive shaft receiving cavity 516 within body 510. Cavity 516 includes a drive shaft 518 best shown in FIGS. 28 and 29. The leading end 506 of handle 500 includes a reamer coupling and drive head 519 adapted to couple to a reamer of the type shown in U.S. Pat. No. 5,658,290. Adjacent the trailing end 504 of handle 500 there is a coupling element such as a threaded bore 520 adapted to couple to end 522 of gripping portion 508. The fully assembled reamer handle 500 is shown in FIG. 27.

Figure 28:
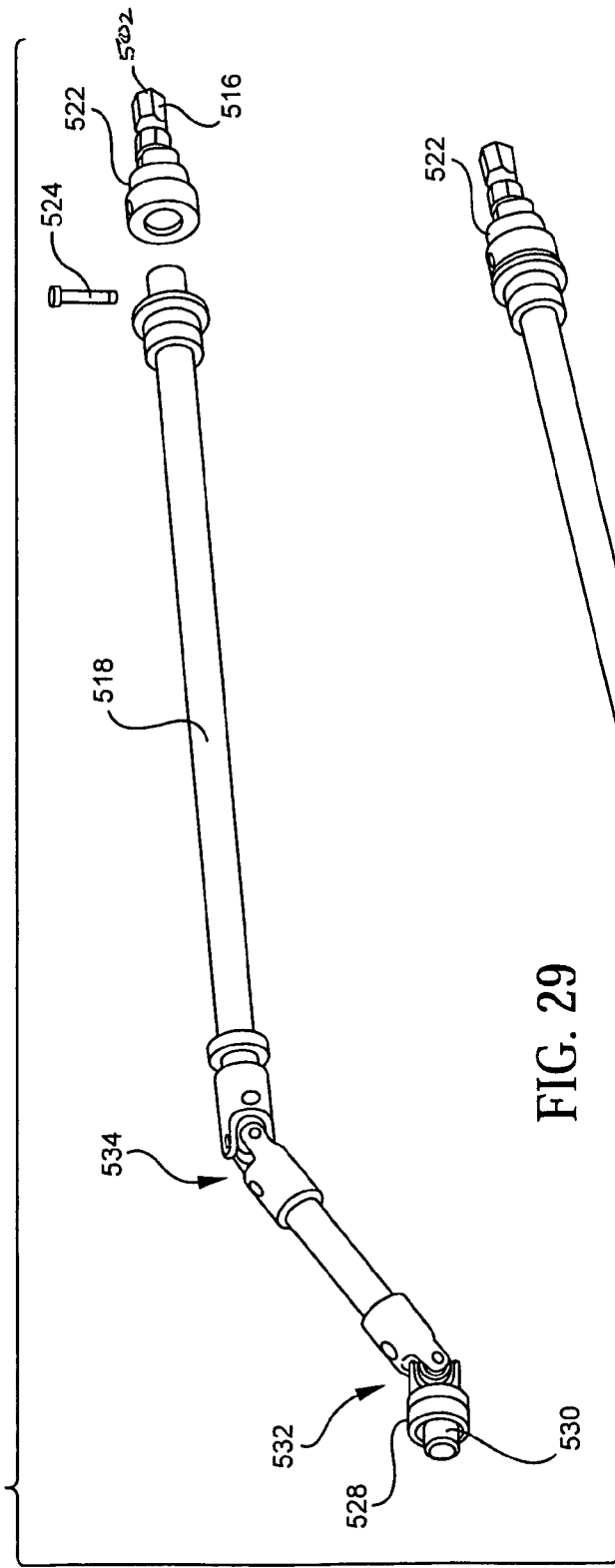
FIG. 28 is a partially exploded view of the drive system for the handle of FIGS. 26 and 27 with a modular drive element detached.
Figure 29:
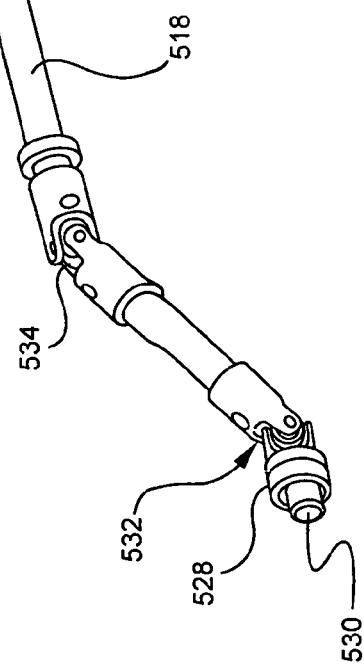
FIG. 29 is an assembled view of the drive system of FIG. 28.
Figure 31:
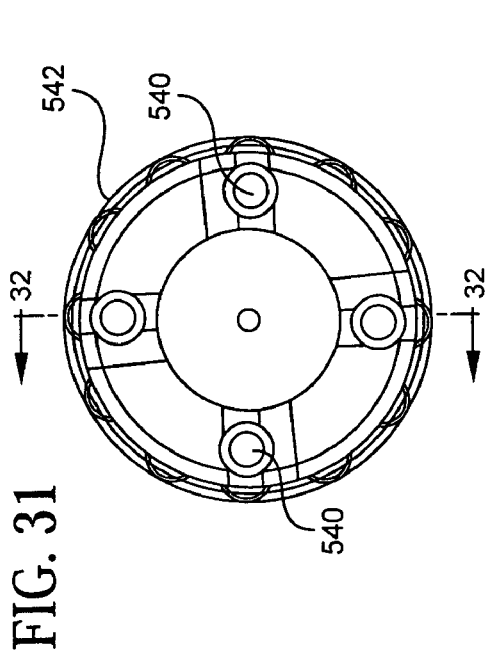
FIG. 31 is an end view of the reamer head of FIG. 30.
Figure 30:
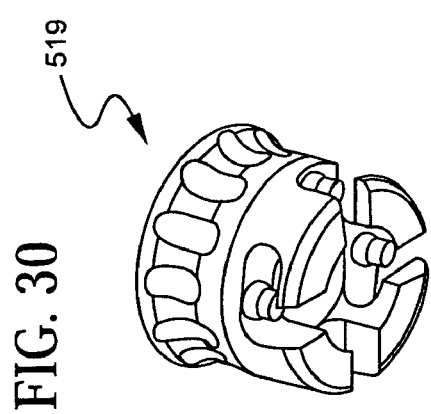
FIG. 30 is an isometric view of the reamer holding head of the reaming handle shown in FIGS. 26 and 27.
Figure 33:
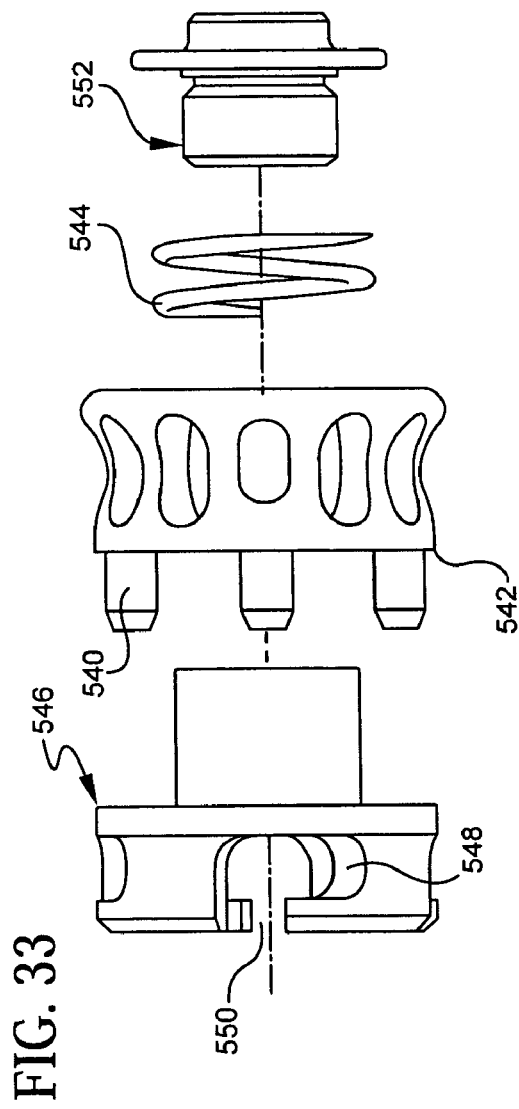
FIG. 33 is an exploded view of the reamer head of FIG. 30.

Drive shaft 518 is shown in FIGS. 28 and 29. FIG. 28 shows the drive shaft 518 with a modular drive system 522, including drive element 502, prior to its assembly to shaft 518. A locking pin 524 is provided to couple modular drive element 522 to the remainder of the shaft 518. In the preferred embodiment, drive element 502 of drive system 522 includes a hex shaped element 526 adapted to mate with any standard power tool such as an electric or pneumatic drill. At a leading end 528 of drive shaft 518 there is a threaded coupling element 530 adapted to engage reamer coupling drive head 519. In the preferred embodiment shaft 18 includes a pair of U-joints 532 and 534 which allows the shaft to make the bends necessary to align it along the offset axis of the handle 500. U-joints 532 and 534 can be of any standard design. In addition modular drive element 522 could be formed integrally with the trailing end of shaft 518.

Figure 32:
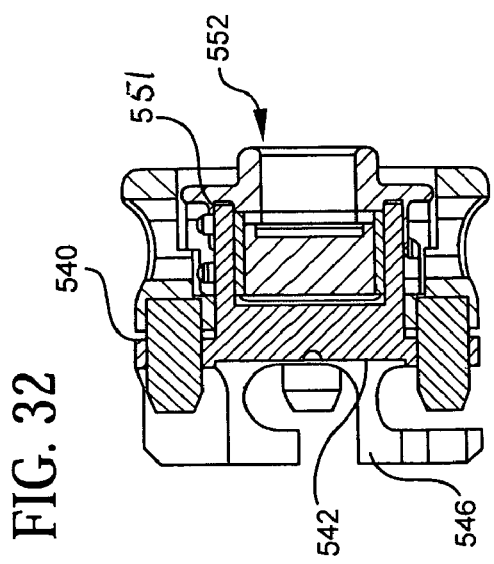
FIG. 32 is a cross-sectional view of the reamer holding head of FIG. 30 along lines 32-32 of FIG. 31.
Figure 34:
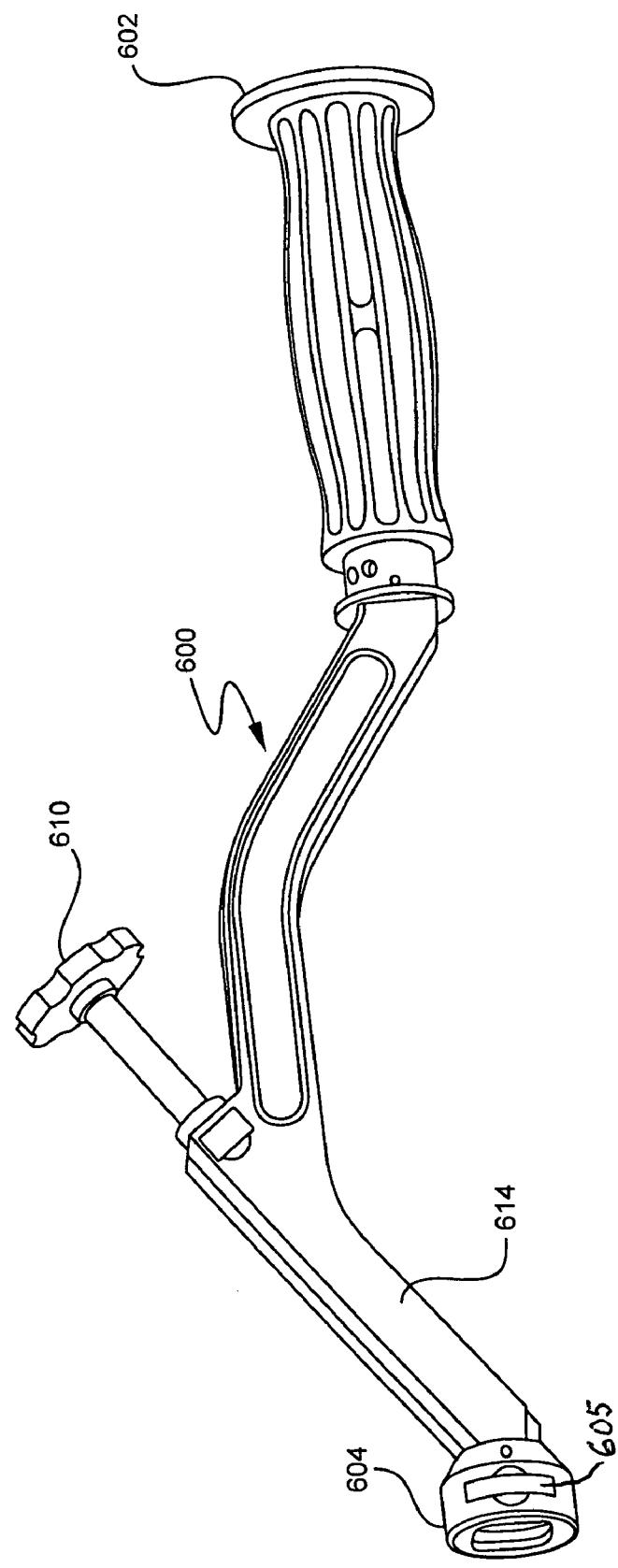
FIG. 34 shows an in-line impactor handle having an impacting plate at a trailing end and a holder or coupling element at its leading end.
Figure 35:
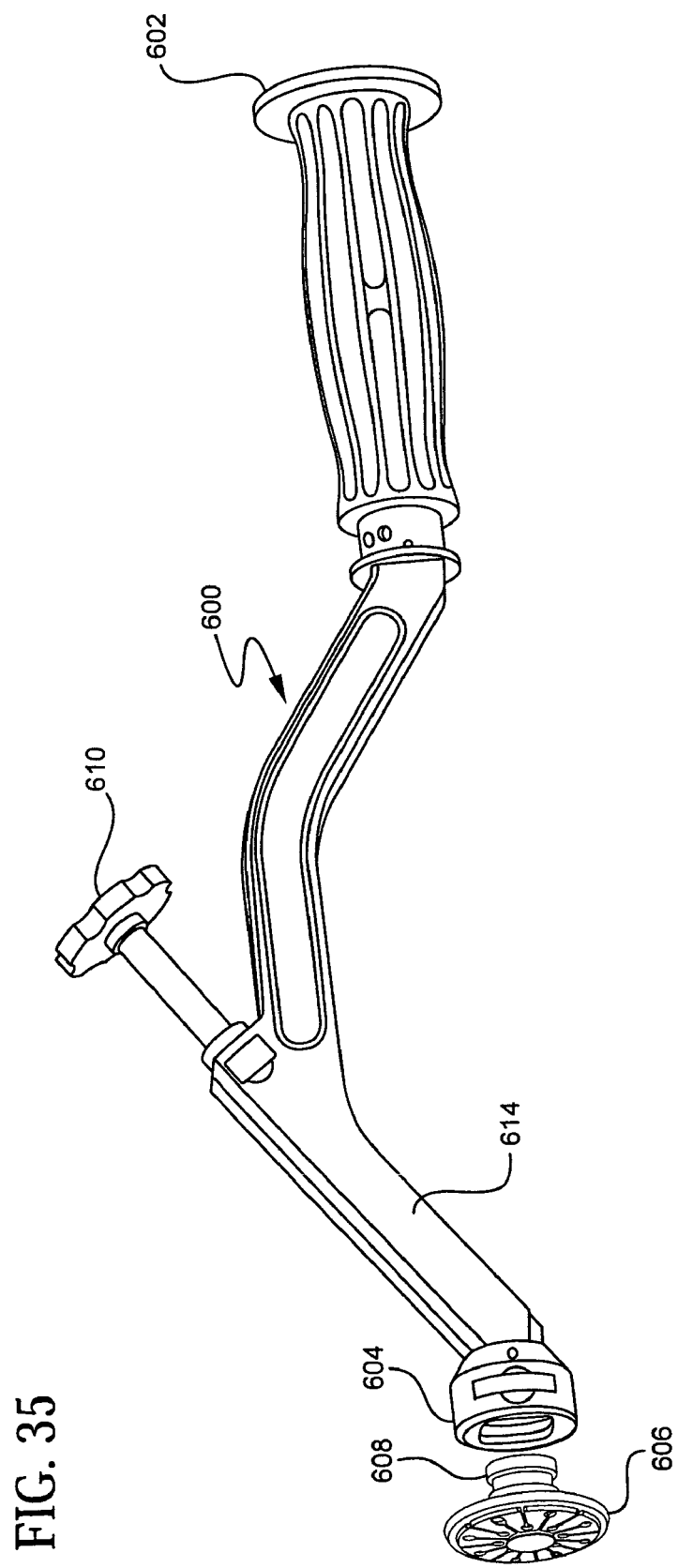
FIG. 35 is a side view of the in-line impactor holder of FIG. 34 prior to the attachment of a coupling element or holder similar to that shown in FIGS. 14 and 15 adapted to be releasably inserted into the leading end of the impactor handle of FIG. 34.
Figure 36:
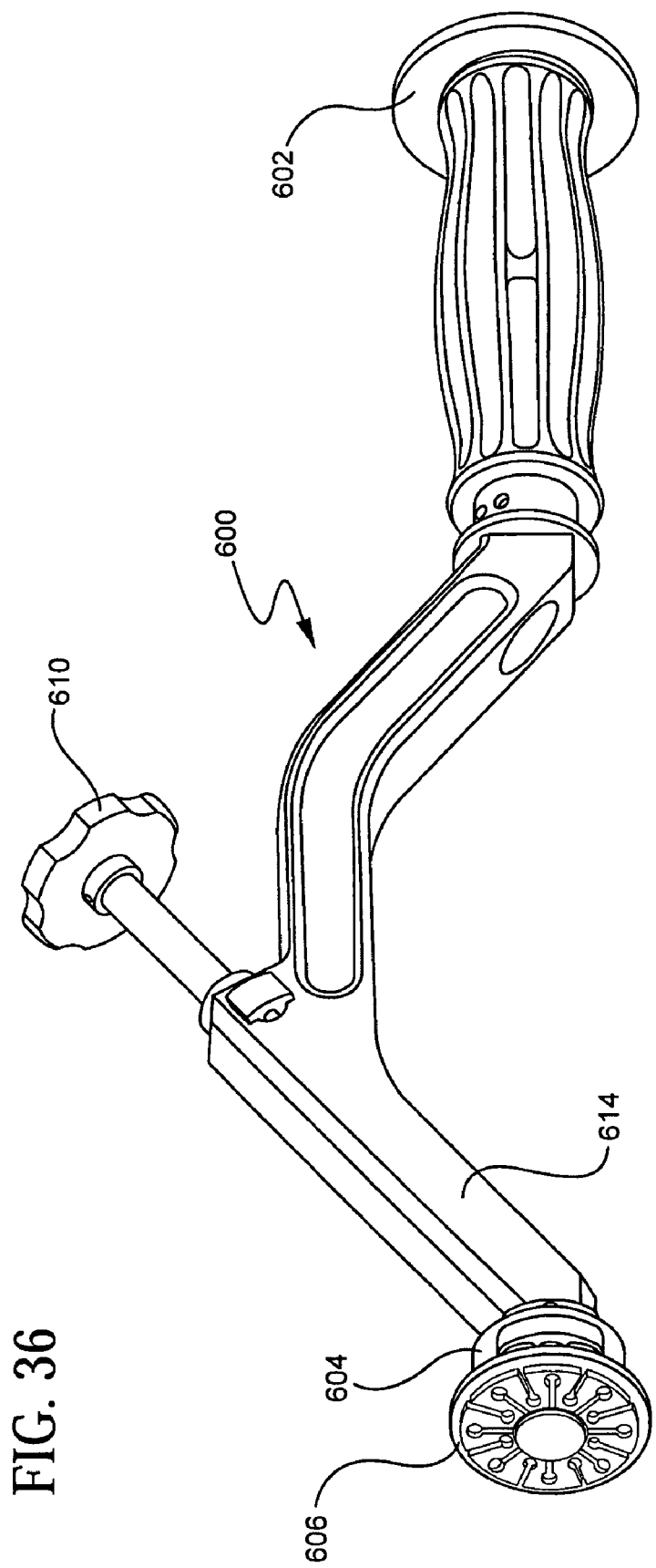
FIG. 36 is an isometric view of the assembled impactor handle of FIG. 34.

Referring to FIGS. 30-33 there is shown reamer drive head assembly 519. Reamer drive head assembly 519 may be assembled to leading end 530 of shaft 518 using any known quick connect mechanism. The drive head includes four posts 540 mounted on a spring loaded sleeve 542. As best shown in FIG. 32 when the head 519 is assembled body sleeve 542 is spring biased by a spring 544 into an extended position where pins 540 engage the cross members of the reamer (not shown). The head assembly also has a bayonet coupling element 546 which, in the preferred embodiment, has four slots 548 each of which have an opening 550 open to the leading end of the coupling and drive head 519. In the preferred embodiment the cross arms of the typical reamer head are inserted through openings 550 and rotated into slots 548. This is accomplished with the spring biased sleeve 542 in a retracted position. When the sleeve 542 is released spring 544 urges the sleeve and pins 540 into engagement with sides of the cross arms to prevent the reamer head from rotating out of slots 548. A threaded flanged element 552 is threaded into a threaded bore within the body 551 of drive head 519 and is adapted to receive the threaded coupling element 530 of shaft 518. A drive head connection mechanism as shown in copending U.S. application Ser. No. 11/342,206 may also be used. The disclosure of application Ser. No. 11/342,206 is incorporated herein by reference.

Figure 37:
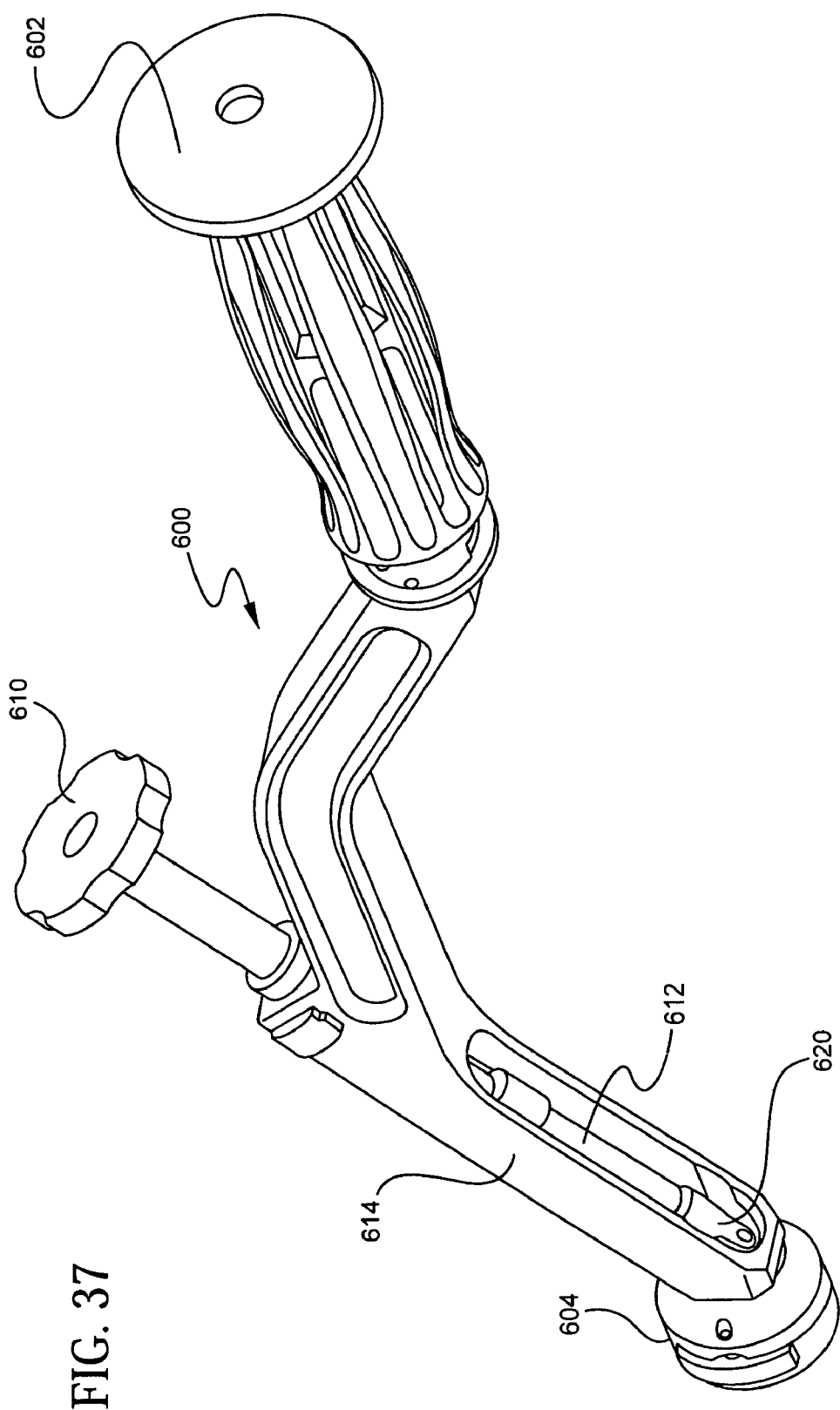
FIG. 37 is a bottom isometric view of the in-line impactor handle of FIG. 34.

Referring to FIGS. 34-37 there is shown an in-line impactor generally denoted as 600 having a trailing end with an impact plate 602 on a leading end with a coupler 604. Coupler 604 is adapted to engage a holder 606 which is similar to the holder of FIGS. 14-15A with the exception that the quick connect mechanisms are located in head assembly 604 rather than on the holder 606. The holder 606 then has a coupling element 608 similar to the coupling element 16 at the leading element of the handle 10 as shown in FIGS. 8 and 9. In other words the coupling elements on the two parts are reversed for the ease of manufacture. As can be seen a single quick connect element can be placed on the handle rather than requiring a plurality of quick connect elements placed within each modular holder a quick release button 605 is provided in coupler 604. A rotatable knob 610 is coupled to a shaft 612, best seen in FIG. 37, mounted within a housing 614 adjacent the leading end of the impacting tool 600. Shaft 612 is connected to a threaded coupling which engages a threaded bore in the holder element 608 to coupled holder 606 to the impactor 600 and to actuate the conical element 106 and 406 of FIGS. 14 and 23 respectively to expand and contract the gripping elements 100 of the holder as discussed with respect to FIGS. 14-15A. Thus, rotation of the knob 610 results in the gripping or releasing of the acetabular cup or insert from holder 606. As can be seen in FIG. 37 shaft 612 includes a single U-joint 620 which allows the axis of the head 604 to be angled with respect to the axis of shaft 612.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup insertion instrument comprising:
a handle portion having a drive shaft therethrough;
a non-linear hollow body portion mounted on a first end of said handle portion, the first end of the handle portion having a first groove open towards the body portion;
a releasable lid connected to at least a portion of said non-linear hollow body, the lid having a tongue portion at a first and second end thereof;
a flexible drive shaft connected to said drive shaft in said handle portion at a first end of said hollow body, an acetabular device holder at a second end of said hollow body, the device holder having a second groove open towards the body portion, the first and second grooves respectively receiving the tongue portions at the first and second ends of the lid, and a spring biased locking element slidably mounted on the acetabular device holder, the locking element spring biased towards the non-linear body portion, the locking element locking the tongue at the second end of the lid within the second groove when in a first position and is slidable with respect to the holder against the spring bias to a second position to allow the release of the tongue from the second groove.

2. The acetabular cup insertion instrument as set forth in claim 1 wherein the flexible shaft comprises at least two U-joints.

3. The acetabular cup insertion instrument as set forth in claim 1 wherein said holder engages a member selected from the group consisting of a reaming tool, a prosthetic acetabular cup, a prosthetic bearing and an outer shell of a prosthetic acetabular cup.

4. The acetabular cup insertion instrument as set forth in claim 1 wherein said non-linear hollow body is curved.

5. The acetabular cup insertion instrument as set forth in claim 4, wherein said releasable lid is curved to match the curved non-linear body and extends for substantially the entire length of said curved hollow body.

6. The acetabular cup insertion instrument as set forth in claim 1 wherein said flexible shaft is a wound wire.

7. The acetabular cup insertion instrument as set forth in claim 1, wherein said holder is expandable.

8. The acetabular cup insertion instrument as set forth in claim 7, wherein said expandable portion is moved radially outwardly by rotating said flexible drive shaft.

9. A holder for an acetabular cup insertion implant comprising:
a body having a central threaded bore extending along an axis;
an expandable collet mounted on the body, said collet having a central bore and two radially extending spring biased arms intersecting the central bore and having curved portions extending towards a periphery of said collet, the radially extending spring biased arms moveable from a first radial position with respect to the central bore to a second radial position spaced further from the central bore wherein said curved portions engage an inner circumference of a rim of an acetabular implant; and
a rotatable element having a threaded portion extending through the bore in said collet and threadably engaging the threaded bore in said body, said rotatable element having a tapered portion for engaging the bore in said collet and moving the radially extending arms against the spring bias towards the second radial position as a wider end of said taper portion engages said bore upon rotation of said rotatable element, and
a releasable lid connected to at least a portion of said body, the lid having a tongue portion at a first and second end thereof;
a flexible drive shaft connected to said driver shaft in said handle portion at a first end of said body, said collet at a second of said body, the collet having a second groove open towards the body portion, the first and second grooves respectively receiving the tongue portions at the first and second ends of the lid.

10. The holder as set forth in claim 9 wherein the two of radially extending arms are separated by slots.

11. The holder as set forth in claim 9 wherein the two radially extending elements are slidably mounted within a track formed in the collet.

12. The holder as set forth in claim 9 wherein said rotatable element has a drive portion for engaging a drive shaft.

13. The acetabular cup insertion instrument as set forth in claim 1 wherein the handle portion has a rotatable element mounted on
an outer surface thereof and rotatable about a longitudinal axis of the handle, the handle portion outer surface including a plurality of detents; and
the rotatable element having an alignment device having alignment elements and having a gripping portion for gripping said outer surface of said handle portion with said plurality of detents, said rotatable element having a detent engagement element selectively engageable with at least one of said plurality of detents on the handle outer surface.

14. The acetabular cup insertion instrument as set forth in claim 13 wherein said non-linear hollow body portion has a curved portion.

15. The acetabular cup insertion instrument as set forth in claim 14 wherein said shaft outer surface with said detents is adjacent a straight portion of said non-linear hollow body portion.

16. The acetabular cup insertion instrument as set forth in claim 13 wherein said detents on said handle portion are bores in said outer surface.

17. The acetabular cup insertion instrument as set forth in claim 16 where said detent engagement element is a pin mounted on said gripping portion and biased into engagement with said bores.

18. The acetabular cup insertion instrument as set forth in claim 17 wherein said gripping portion includes a means for moving said pin against said biasing and out of engagement with said bores.

19. The acetabular cup insertion instrument of claim 1 wherein a central longitudinal axis of said handle portion is parallel to and offset from a central longitudinal axis of said acetabular device holder.

* * * * *

UNITED STATES PATENT AND TRADEMARK OFFICE
CERTIFICATE OF CORRECTION

PATENT NO. : 7,993,348 B2
APPLICATION NO. : 11/641599
DATED : August 9, 2011
INVENTOR(S) : John Conte and Joseph C. Jenkins, II It is certified that error appears in the above-identified patent and that said Letters Patent is hereby corrected as shown below:

In the Specification

Column 2, line 2, "curved" should read --curve--
Column 2, line 11, after "into" insert --an--
Column 2, line 34, "needs" should read --need--
Column 2, line 43, "u-joints" should read --U-joints--
Column 3, line 10, after "connected" insert --to--
Column 3, line 47, "composing" should read --composed--
Column 4, line 20, "open curved" should read --open-curved--
Column 5, line 13, "collect" should read --collected--
Column 6, line 10, after "position" insert --the--
Column 6, line 21, replace "is" with --are--
Column 7, line 18, "spring biased" should read --spring-biased--
Column 6, line 27, replace "a" with --an--
Column 7, line 52, "reamer holding" should read --reamer-holding--
Column 7, line 55, "reamer holding" should read --reamer-holding--
Column 8, line 18, "u-joint" should read --U-Joint--
Column 8, line 45, "u-joint" should read --U-Joint--
Column 9, line 14, "utilize" should read --utilizes--
Column 9, line 14, "spring loaded" should read --spring-loaded--
Column 9, line 44, "Button" should read --button--
Column 9, line 59, after "perimeter" insert --of--
Column 10, line 25, "spring biased" should read --spring-biased--
Column 10, line 50, replace "is" with --are--
Column 10, line 63, "spring loaded" should read --spring-loaded--
Column 11, line 16, replace "a" with --an--
Column 11, line 66, "hex shaped" should read --hex-shaped--
Column 12, line 14, "spring loaded" should read --spring-loaded--
Column 12, line 16, "spring biased" should be --spring-biased--
Column 12, line 20, "have" should read --has--

Signed and Sealed this
Nineteenth Day of November, 2013

Teresa Stanek Rea
*Deputy Director of the United States Patent and Trademark Office*

CERTIFICATE OF CORRECTION (continued)
U.S. Pat. No. 7,993,348 B2

In the Claims

Column 13, line 19, "spring biased" should be --spring-biased--
Column 13, line 21, "spring biased" should be --spring-biased--
Column 13, line 52, "spring biased" should be --spring-biased--
Column 13, line 55, "spring biased" should be --spring-biased--
Column 14, line 12, "driver" should read --drive--
Column 14, line 14, after "second" insert --end--
Column 14, line 18, after "two" delete "of"